United States Patent
Matsumoto et al.

(10) Patent No.: US 11,199,541 B2
(45) Date of Patent: Dec. 14, 2021

(54) METHOD FOR ANALYZING CELL, CHIP FOR CELL ANALYSIS, REAGENT FOR CELL ANALYSIS, KIT FOR CELL ANALYSIS, AND APPARATUS FOR CELL ANALYSIS

(71) Applicant: Sony Corporation, Tokyo (JP)

(72) Inventors: Masahiro Matsumoto, Kanagawa (JP); Masataka Shinoda, Kanagawa (JP); Yuuki Watanabe, Kanagawa (JP)

(73) Assignee: Sony Corporation, Tokyo (JP)

( * ) Notice: Subject to any disclaimer, the term of this patent is extended or adjusted under 35 U.S.C. 154(b) by 541 days.

(21) Appl. No.: 16/065,947

(22) PCT Filed: Aug. 4, 2016

(86) PCT No.: PCT/JP2016/003608
§ 371 (c)(1),
(2) Date: Jun. 25, 2018

(87) PCT Pub. No.: WO2017/056362
PCT Pub. Date: Apr. 6, 2017

(65) Prior Publication Data
US 2018/0372741 A1 Dec. 27, 2018

(30) Foreign Application Priority Data
Sep. 30, 2015 (JP) .............................. JP2015-193887

(51) Int. Cl.
*G01N 33/569* (2006.01)
*G01N 33/532* (2006.01)
*G01N 33/53* (2006.01)

(52) U.S. Cl.
CPC ......... *G01N 33/569* (2013.01); *G01N 33/532* (2013.01); *G01N 33/5306* (2013.01); *G01N 33/56966* (2013.01)

(58) Field of Classification Search
CPC ............. G01N 33/569; G01N 33/5306; G01N 33/532; G01N 33/533; G01N 33/56966;
(Continued)

(56) References Cited

U.S. PATENT DOCUMENTS

| | | | |
|---|---|---|---|
| 2011/0070605 A1* | 3/2011 | Busch | ............ G01N 33/56972 435/34 |
| 2014/0134645 A1 | 5/2014 | Lee et al. | |
| 2016/0327580 A1* | 11/2016 | Burger-Kentischer | ..................... G01N 33/92 |

FOREIGN PATENT DOCUMENTS

| | | |
|---|---|---|
| JP | 09-501830 A | 2/1997 |
| JP | 2005-511058 A | 4/2005 |

(Continued)

OTHER PUBLICATIONS

International Search Report and Written Opinion dated Dec. 19, 2016 in connection with International Application No. PCT/JP2016/003608.

(Continued)

*Primary Examiner* — Gailene Gabel
(74) *Attorney, Agent, or Firm* — Wolf, Greenfield & Sacks, P.C.

(57) ABSTRACT

According to some aspects, a method for analyzing a cell is provided. The method includes trapping the cell by binding a first molecule to the cell. The method further includes binding a second molecule to the cell. The second molecule includes a binding portion capable of specific binding to a cell-surface molecule of the cell. The second molecule further includes an identifying portion, a labeling portion coupled to the identifying portion, and a stimulus-degradable linker between the binding portion and the identification portion. The method further includes detaching the identifying portion from the binding portion by stimulating the stimulus-degradable linker where the detached identifying portion is coupled to the labeling portion. The method further includes binding the detached identifying portion through specific binding to an identifying portion recognizing molecule and detecting the labeling portion.

13 Claims, 17 Drawing Sheets

(58) Field of Classification Search
CPC ......... G01N 33/56977; G01N 33/6854; G01N 33/6872
See application file for complete search history.

(56) References Cited

FOREIGN PATENT DOCUMENTS

| | | |
|---|---|---|
| JP | 2008-253176 A | 10/2008 |
| JP | 2014-073092 A | 4/2014 |
| WO | 02/054065 A2 | 7/2002 |

OTHER PUBLICATIONS

International Preliminary Report on Patentability dated Apr. 12, 2018 in connection with International Application No. PCT/JP2016/003608.
Ullal et al., Cancer Cell Profiling by Barcoding Allows Multiplexed Protein Analysis in Fine Needle Aspirates, Science Translational Medicine, 2014, vol. 6, Issue 219, 219ra9, 13 pages.
Japanese Office Action dated Oct. 29, 2019 in connection with Japanese Application No. 2015-193887 and English translation thereof.

* cited by examiner

[Fig. 1]
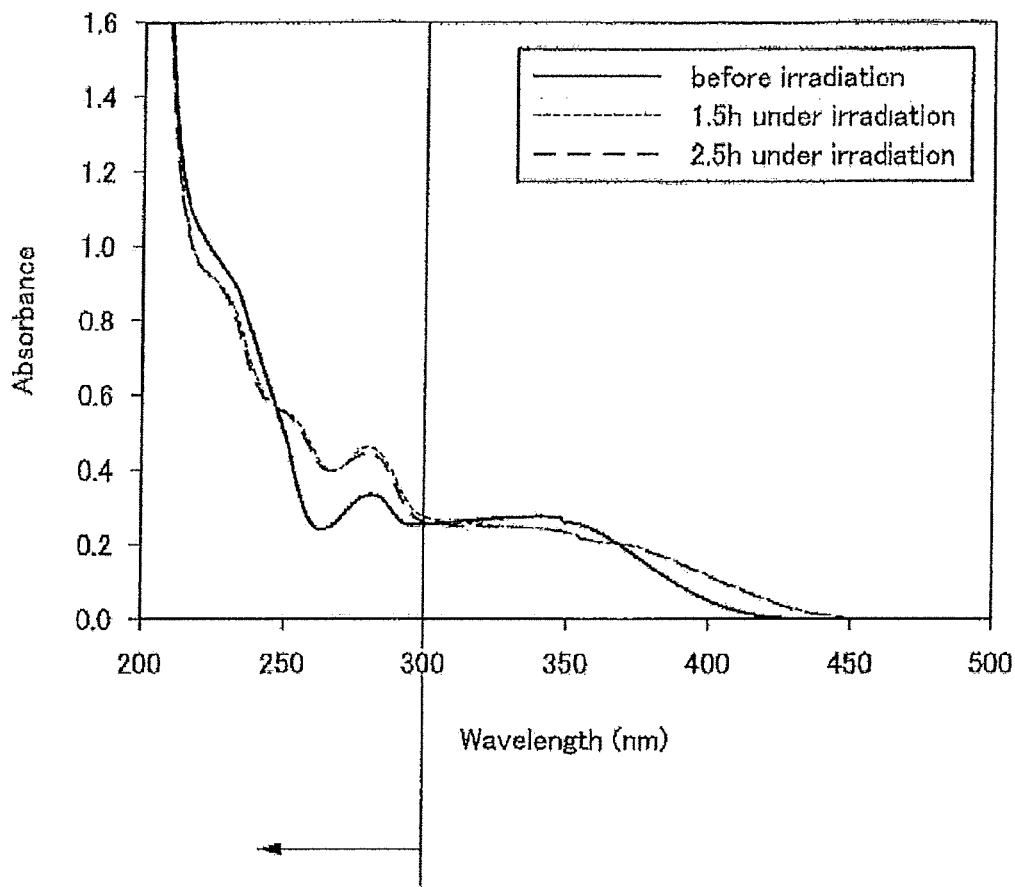
[Fig. 2]
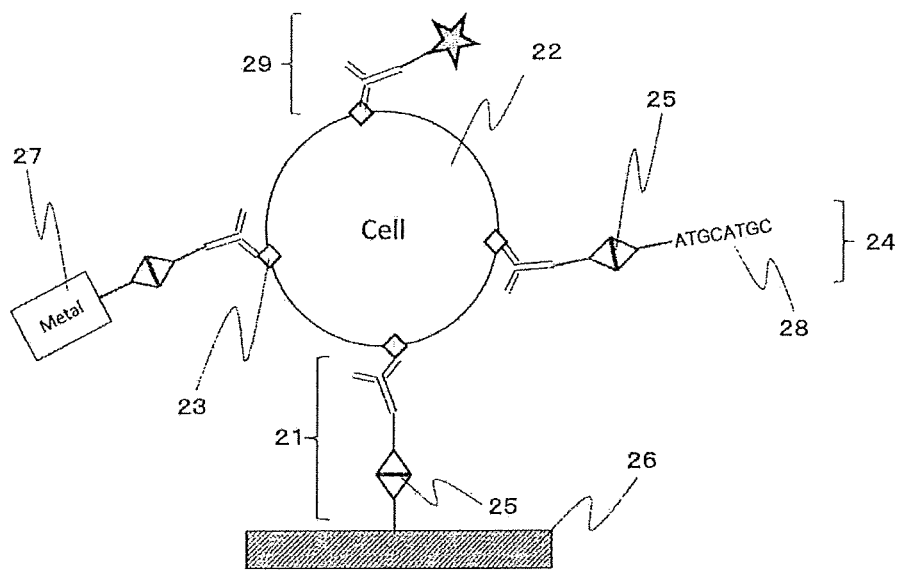

[Fig. 3]
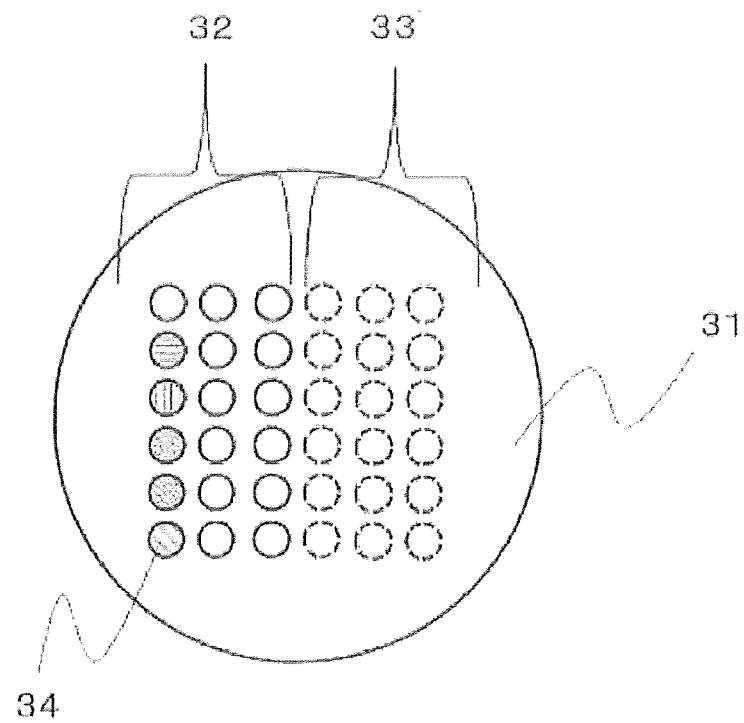
[Fig. 4]
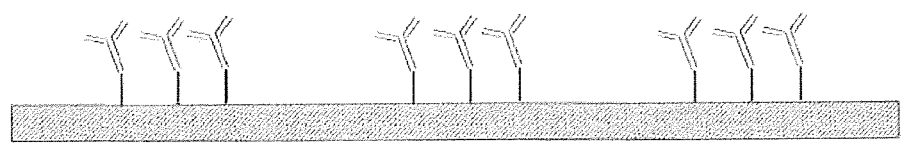
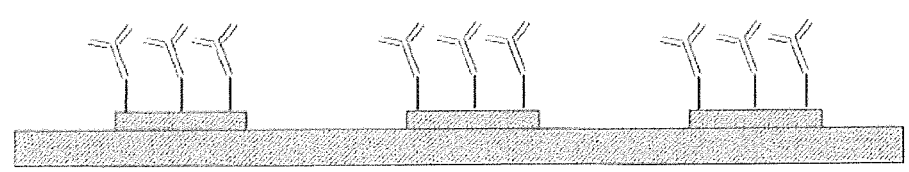
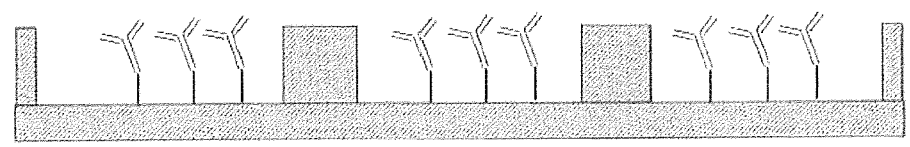

[Fig. 5]
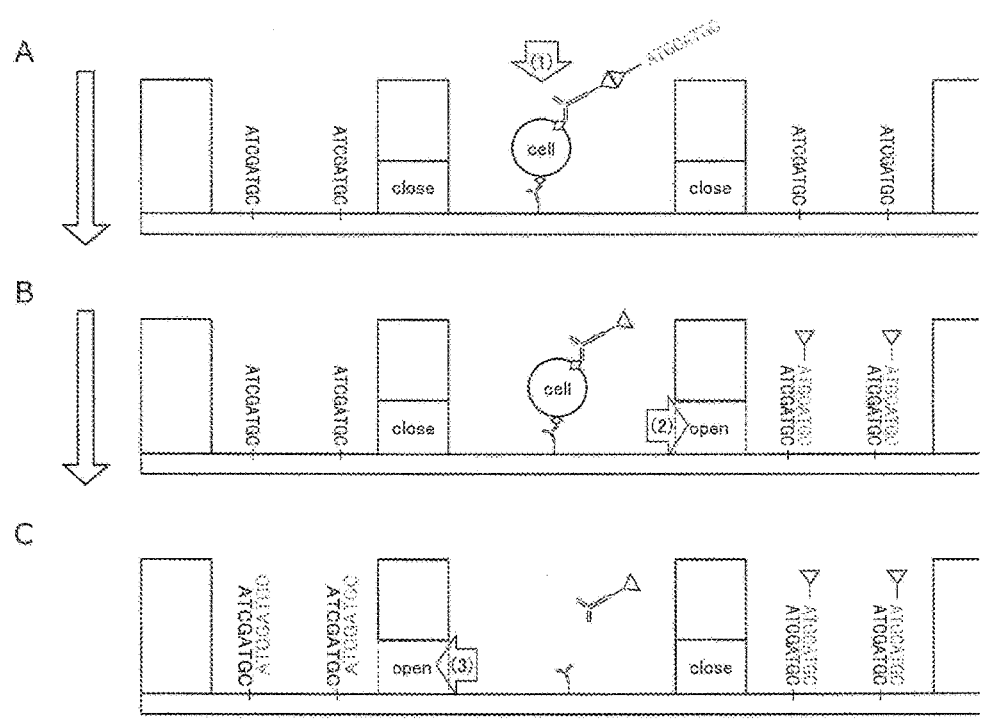
[Fig. 6]
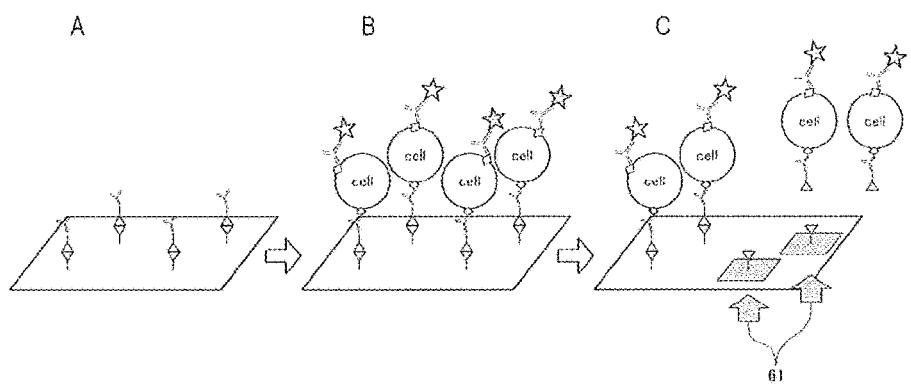

[Fig. 7]
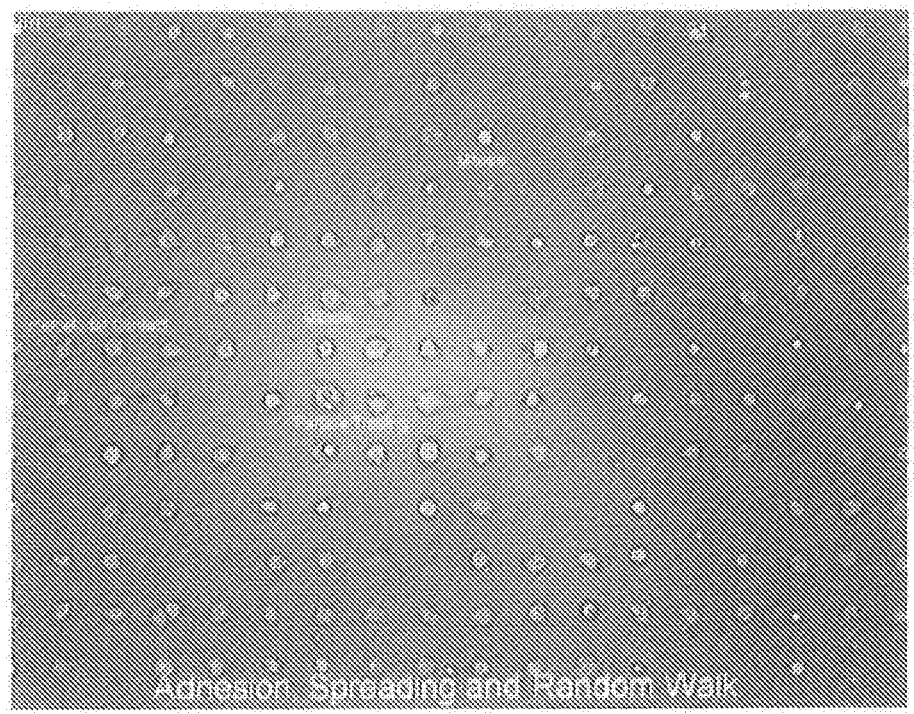
[Fig. 8]
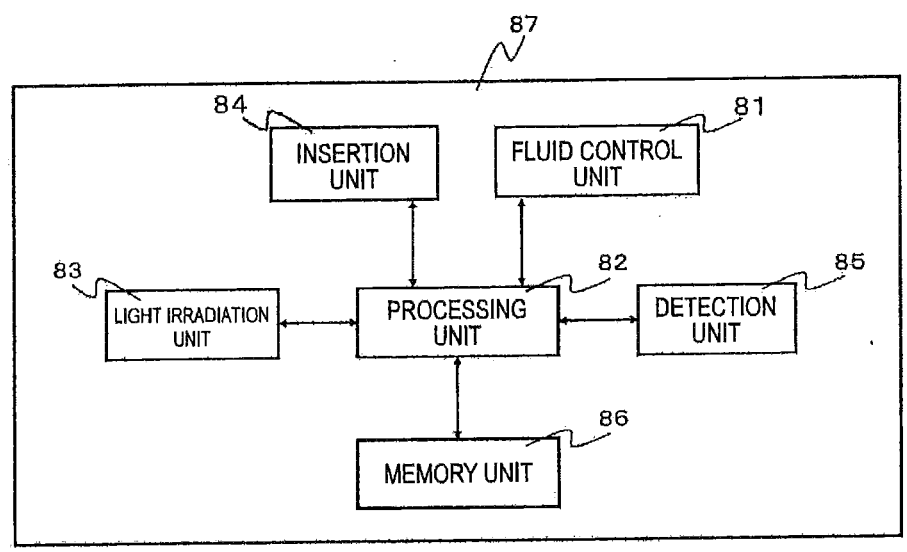

[Fig. 9]
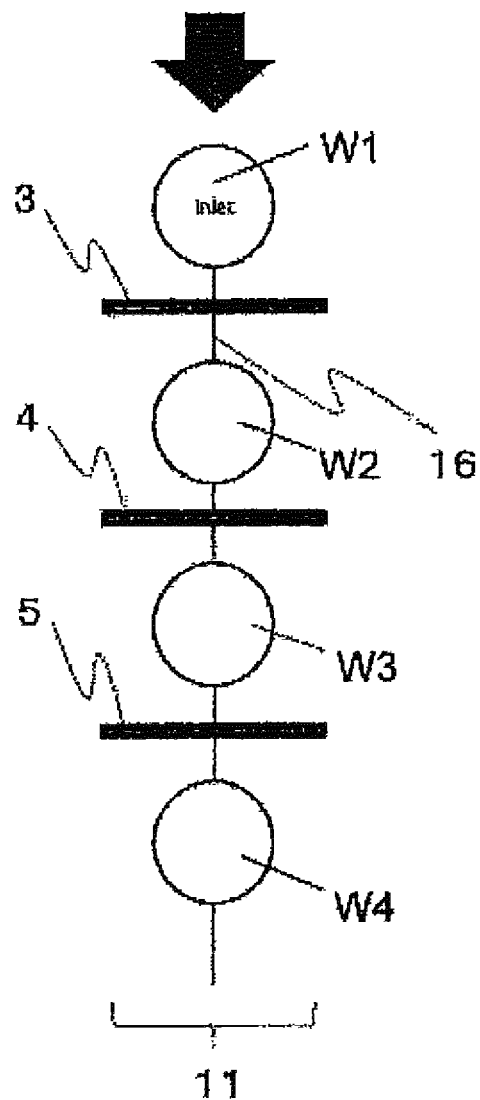

[Fig. 10]
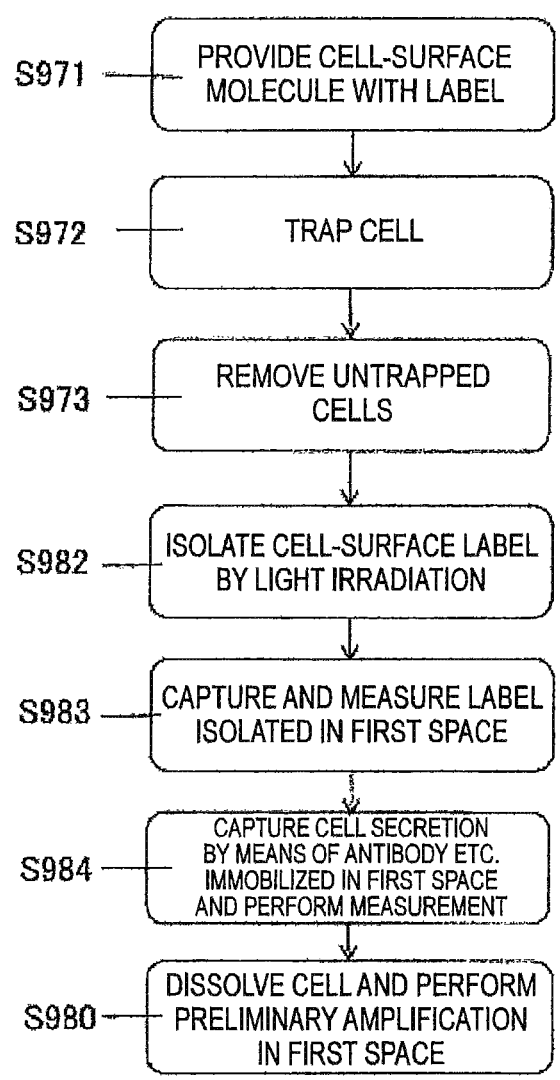

[Fig. 11]
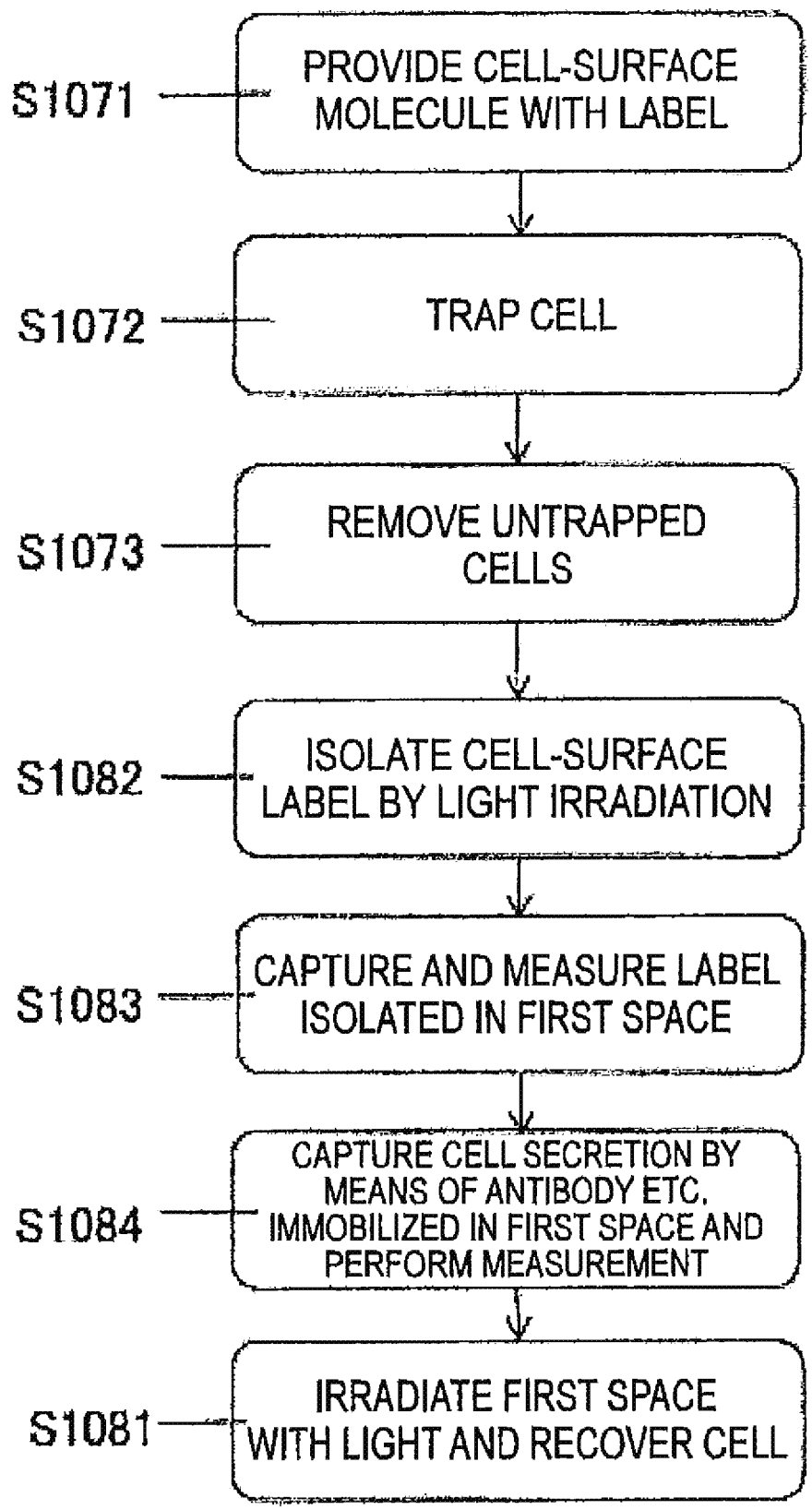

[Fig. 12]
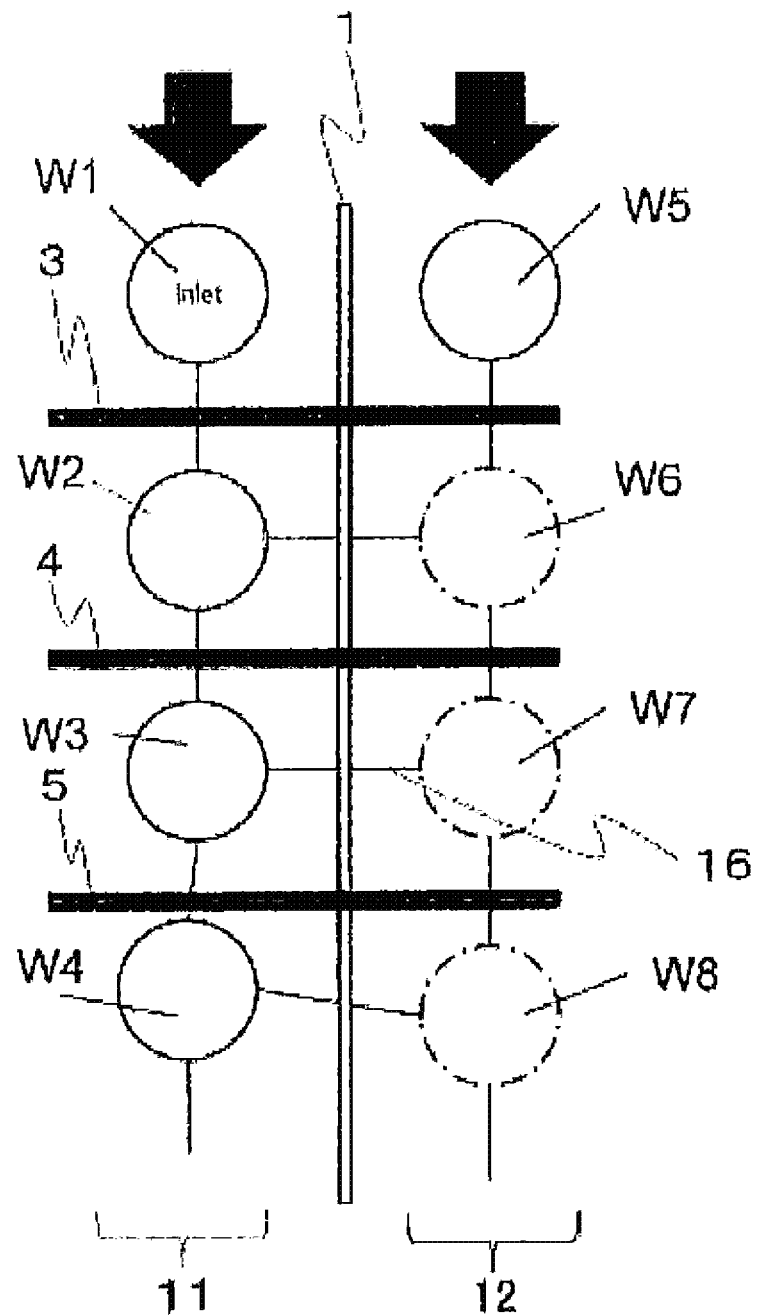

[Fig. 13]
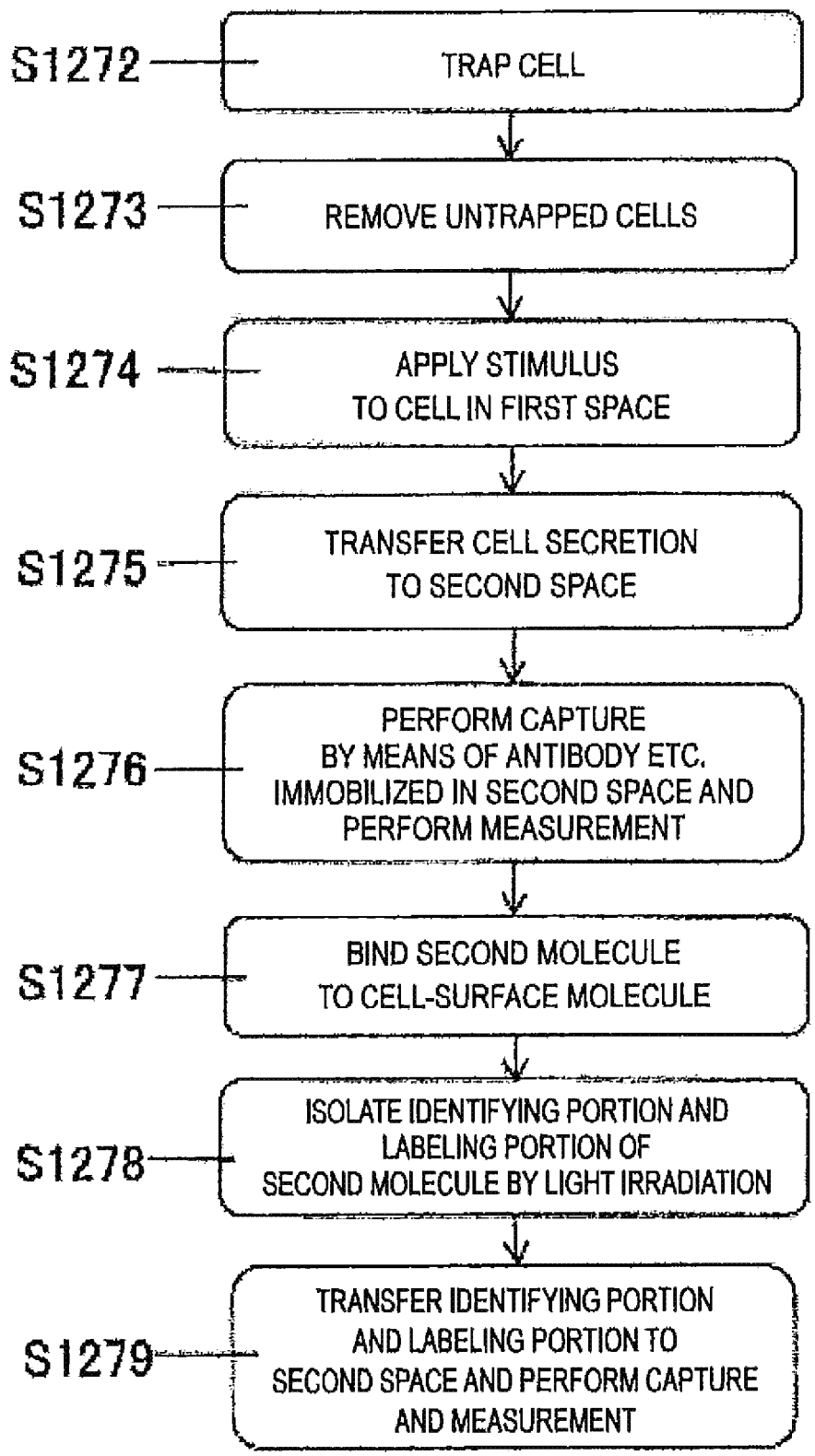

[Fig. 14]
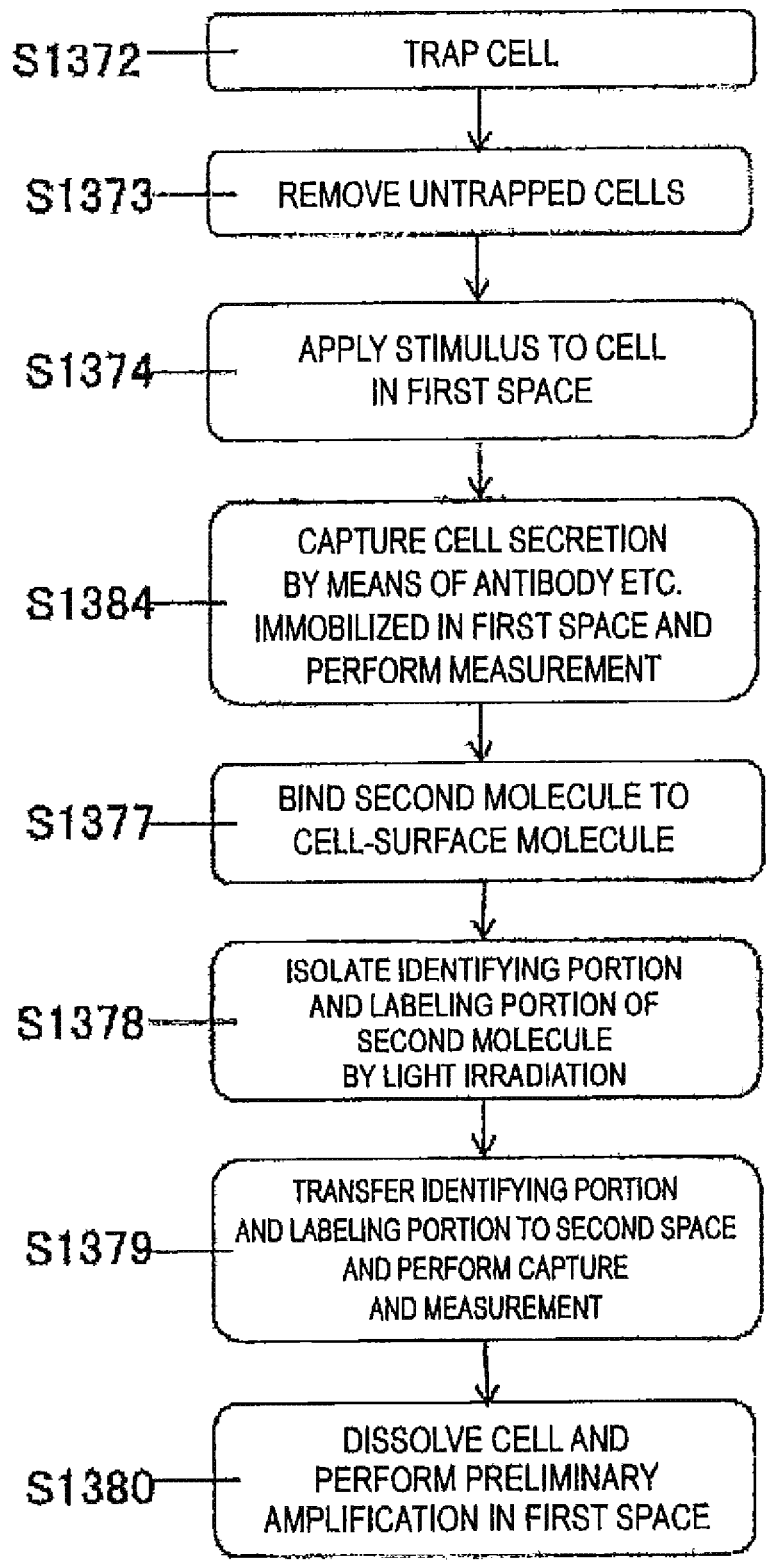

[Fig. 15]
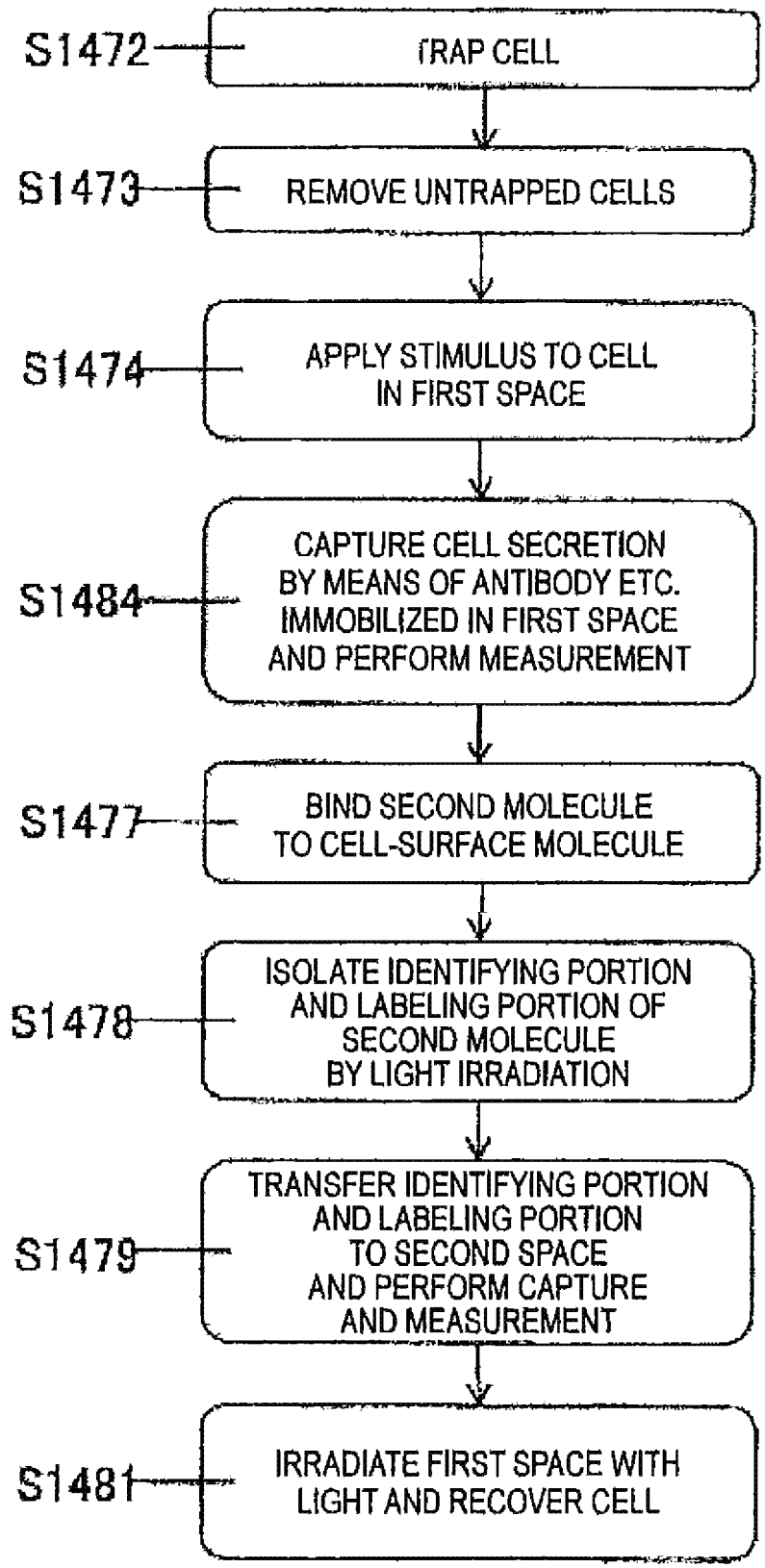

[Fig. 16]
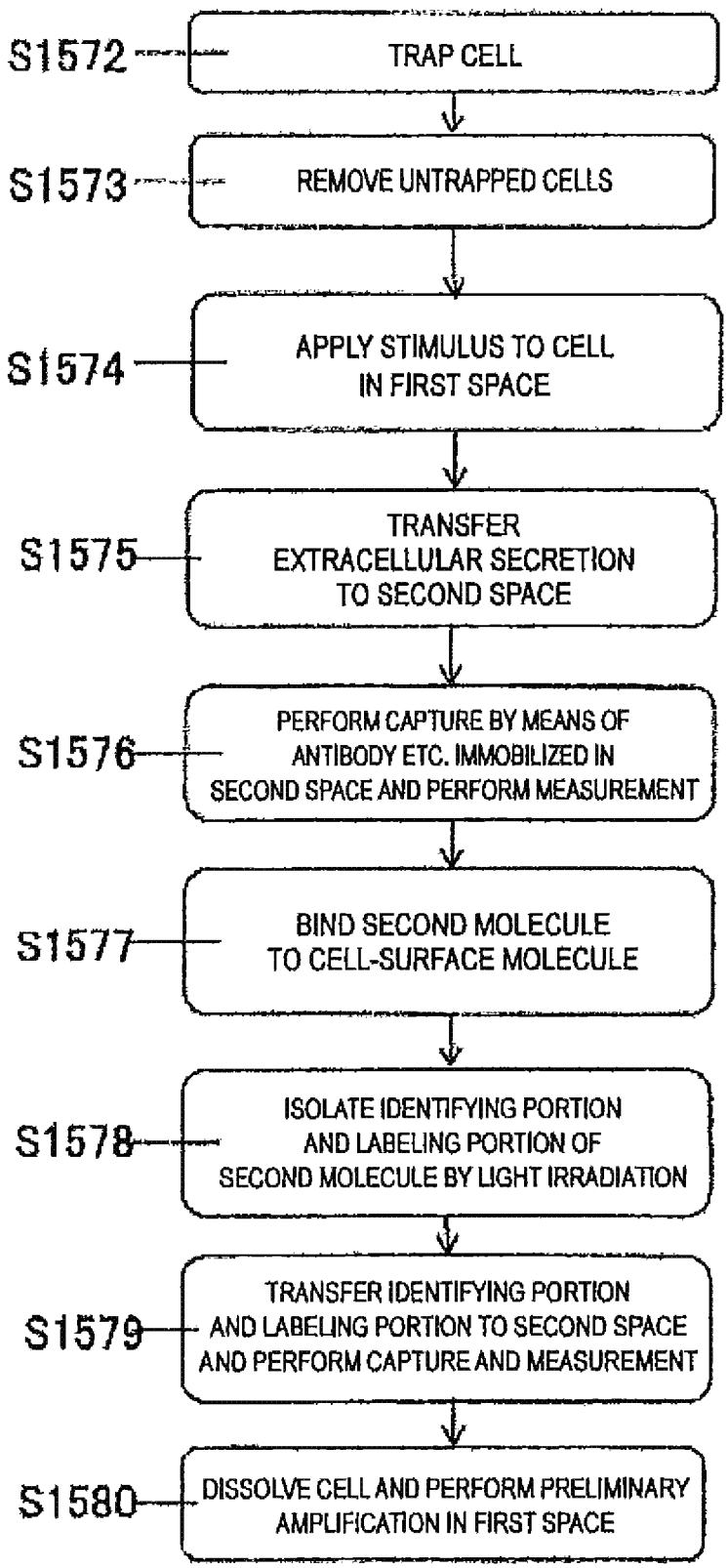

[Fig. 17]
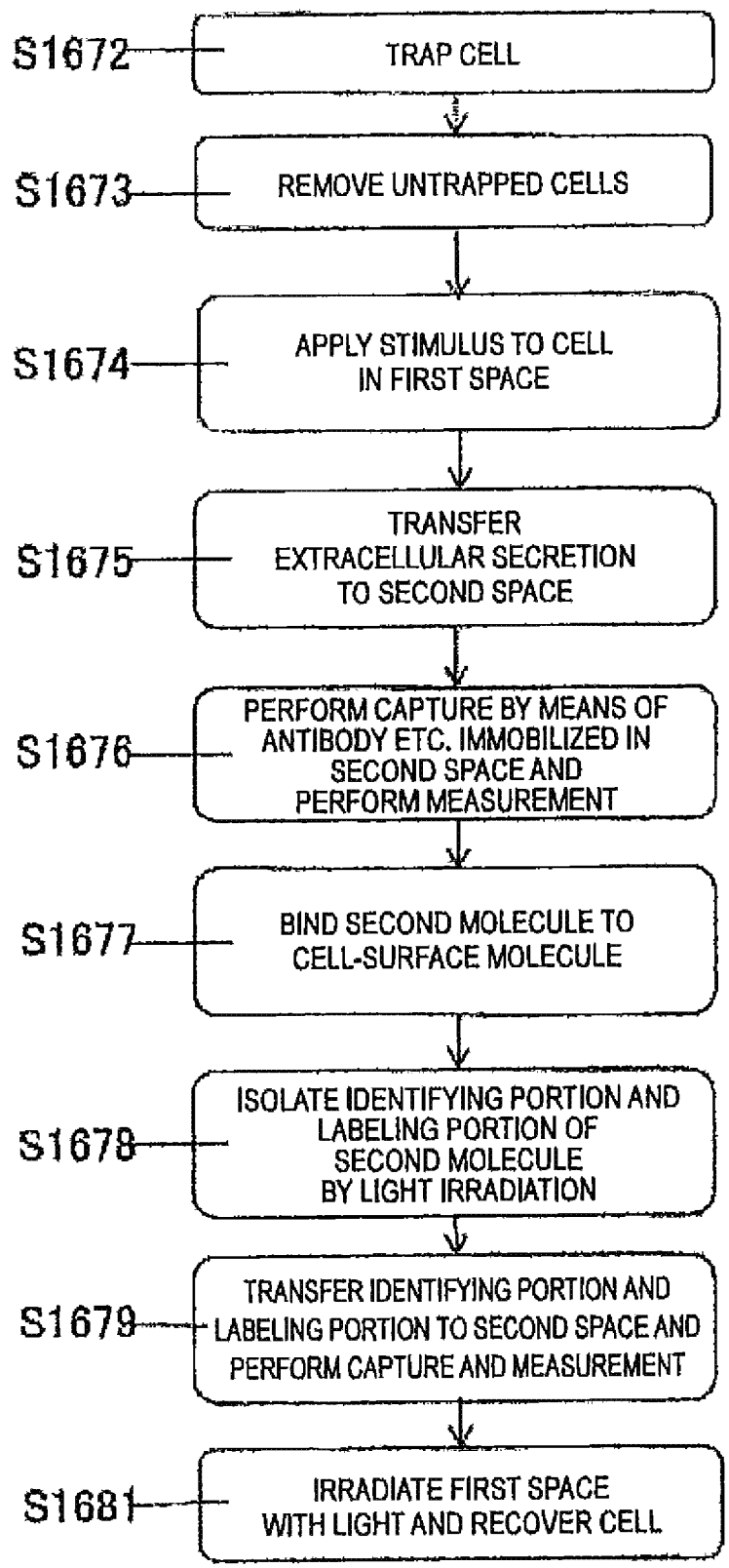

[Fig. 18]
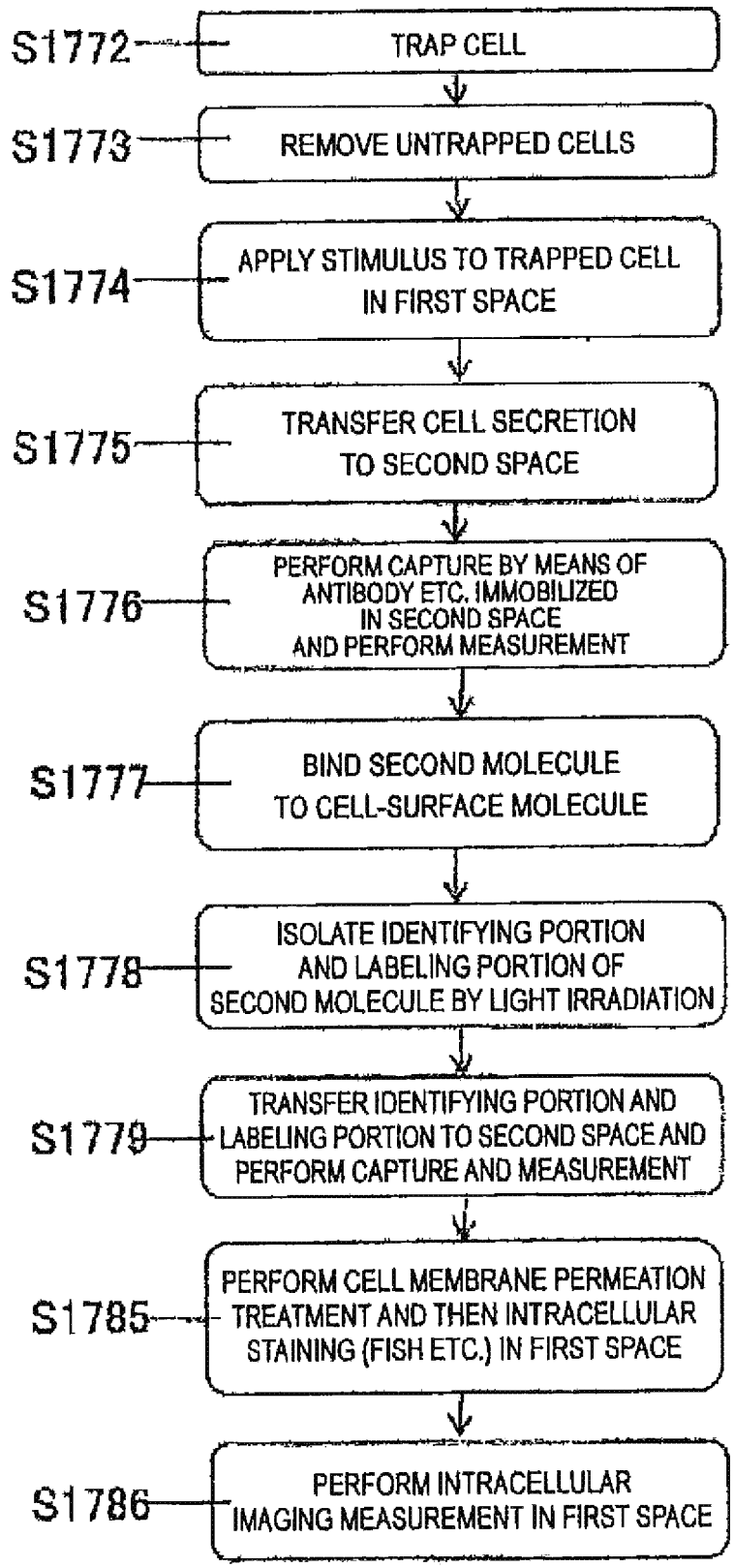

[Fig. 19]
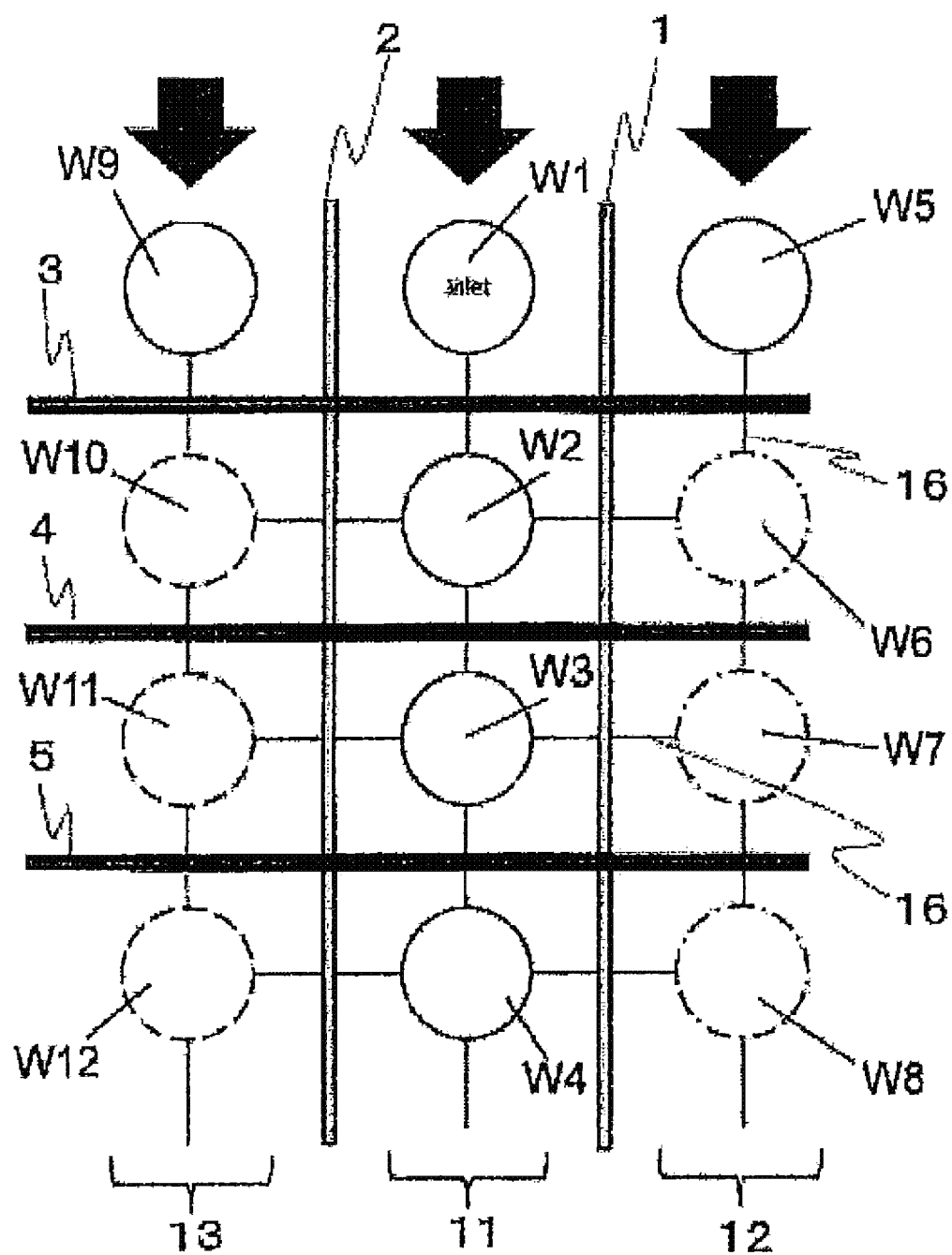

[Fig. 20]
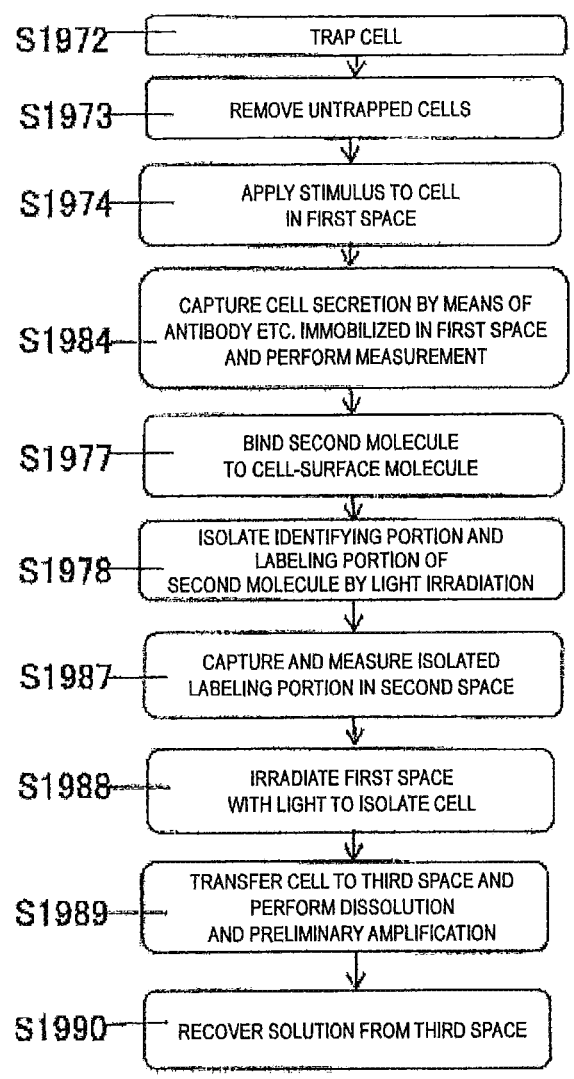

[Fig. 21]
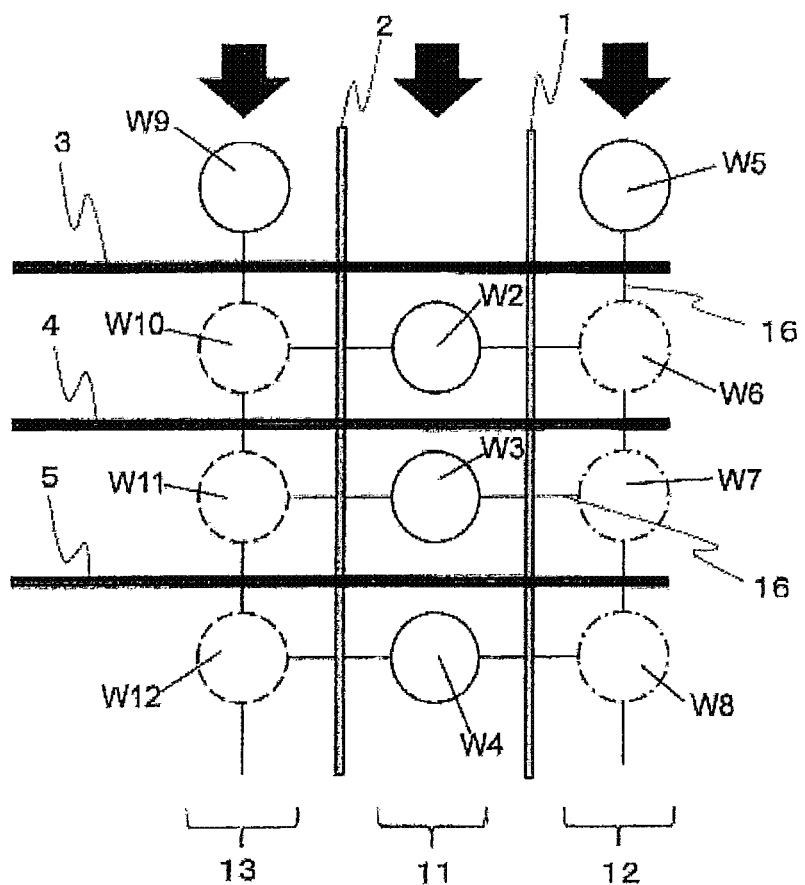

METHOD FOR ANALYZING CELL, CHIP FOR CELL ANALYSIS, REAGENT FOR CELL ANALYSIS, KIT FOR CELL ANALYSIS, AND APPARATUS FOR CELL ANALYSIS

CROSS REFERENCE TO RELATED APPLICATIONS

This application is a national stage entry filed under 35 U.S.C. § 371 of PCT Application Serial No. PCT/JP2016/003608, filed on Aug. 4, 2016. PCT Application Serial No. PCT/JP2016/003608 claims priority to Japanese Priority Patent Application JP 2015-193887 filed Sep. 30, 2015, which is incorporated herein by reference in its entirety.

TECHNICAL FIELD

The present technology relates to a method for analyzing a cell, a chip for cell analysis, a reagent for cell analysis, a kit for cell analysis, and an apparatus for cell analysis. More specifically, the present technology relates particularly also to a method for analyzing a single cell, a chip for single-cell analysis, a reagent for single-cell analysis, a kit for single-cell analysis, and an apparatus for single-cell analysis.

BACKGROUND ART

The single-cell analysis in related art has remained analyses taking a limited number of specific genes as a target, such as flow cytometry, or protein analyses using mass cytometry technology.

The flow cytometry is a method in which, while cells in each of which an antibody with a fluorochrome bound thereto and a cell-surface antigen are specifically bound are passed at high speed one by one, the fluorochrome is excited with a laser or the like and the fluorescence is measured.

However, although multicolor detection is possible by using a plurality of lasers, only up to 11 colors have been reported as the number of simultaneously measurable colors, due to the complexity of the leakage correction between fluorochromes (the overlapping of fluorescence wavelengths) etc. Furthermore, there has been a problem that the apparatus is expensive because of the installation of a plurality of lasers.

The mass cytometry is a method in which an antibody labeled with a metal isotope is bound to each of cells, and then the cells are destroyed while being passed one by one and the metal isotope is detected by TOF-MS.

However, although 35 types of cell-surface antigens can be measured by using this method, the cell is destroyed during measurement. Hence, it has been unable to obtain the information of the contents of the cell (DNA, RNA, etc.). Furthermore, the cell has been unable to be sent to other processes such as culture.

Separately from the methods mentioned above, a group of Massachusetts General Hospital has recently performed a comprehensive analysis of cell-surface antigens. In the analysis, an nCounter instrument of NanoString Technologies, Inc. and a photodegradable linker are used (NPL 1).

However, in this method, although the surface antigen is measured comprehensively, the information of the contents of the cell has not yet been obtained. Furthermore, after the fluorescent barcode-labeled antibody bound to the surface antigen is isolated by the photodegradable linker, the antibody needs to be transferred to another plate and measured; hence, the method has not been suitable for the measurement of a large number of cells.

As the photodegradable linker usable in the method mentioned above, for example, one based on an o-nitrobenzyl compound, one based on a nitroveratryl compound (PTL 1), a parahydroxyphenacyl group, a 7-nitroindoline group, a 2-(2-nitrophenyl)ethyl group, a (coumarin-4-yl)methyl group, etc. (PTL 2) have been given.

CITATION LIST

Patent Literature

PTL 1: JP 2005-511058A
PTL 2: JP 2014-73092A

Non Patent Literature

NPL 1: A. V. Ullall, et al., "Cancer Cell Profiling by Barcoding Allows Multiplexed Protein Analysis in Fine-Needle Aspirates", Science Translational Medicine, 2014, Vol. 6, Issue 219, pp. 219ra9

SUMMARY

Technical Problem

It is desirable to perform a comprehensive analysis of a cell in which the cell is analyzed without being destroyed and also the information of the contents of the cell is obtained, in view of the issues of the flow cytometry and the mass cytometry described above, etc. The comprehensive analysis includes, for example, obtaining the information of cell-surface molecules, cell secretions, intracellular molecules, etc. in a single cell or a plurality of cells.

Solution to Problem

According to an aspect of the present application, a method for analyzing a cell is provided. The method includes trapping the cell by binding a first molecule to the cell and binding a second molecule to the cell. The second molecule includes a binding portion capable of specific binding to a cell-surface molecule of the cell, an identifying portion, a labeling portion coupled to the identifying portion, and a stimulus-degradable linker between the binding portion and the identification portion. The method further includes detaching the identifying portion from the binding portion by stimulating the stimulus-degradable linker. The detached identifying portion is coupled to the labeling portion. The method further includes binding the detached identifying portion through specific binding to an identifying portion recognizing molecule and detecting the labeling portion.

According to an aspect of the present application, a chip for cell analysis is provided. The chip includes a first region where a first molecule capable of binding to a cell is immobilized. The chip further includes a second region where an identifying portion recognizing molecule is immobilized. The identifying portion recognizing molecule is capable of binding specifically to a second molecule having an identifying portion and a labeling portion that identify information about the cell. The chip further includes a detection region configured to detect the labeling portion.

According to an aspect of the present application, a reagent for cell analysis is provided. The reagent includes a molecule that includes a binding portion capable of binding specifically to a molecule selected from the group consisting of a cell-surface molecule, an intracellular molecule, and a cell secretion. The molecule further includes an identifying portion, a labeling portion coupled to the identifying portion, and a stimulus-degradable linker between the binding portion and the identification portion.

According to an aspect of the present application, a kit for cell analysis is provided. The kit includes a chip for cell analysis that includes a first region where a first molecule capable of binding to a cell is immobilized. The chip further includes a second region where a molecule capable of binding specifically to a second molecule in which a binding portion capable of binding specifically to the cell, an identifying portion, and a labeling portion are linked is immobilized. The chip further includes a detection region where the labeling portion is able to be detected. The kit further includes a a reagent selected from the group consisting of a reagent containing a molecule including a binding portion capable of binding specifically to a molecule selected from the group consisting of a cell-surface molecule, an intracellular molecule, and a cell secretion and a labeling portion, a reagent that detects the labeling portion of the preceding reagent, and a reagent containing a substance that stimulates cell secretion.

According to an aspect of the present application, an apparatus for cell analysis is provided. The apparatus includes an insertion unit configured to insert a chip for chip analysis. The apparatus further includes a fluid control unit configured to control a movement of a fluid within the chip for cell analysis. The apparatus further includes a light irradiation unit configured to apply light to the first region of the chip for cell analysis. The apparatus further includes a detection unit configured to detect the labeling portion in the detection region of the chip for cell analysis.

Advantageous Effects of Invention

According to an embodiment of the present technology, a large number of cell-surface molecules can be detected simultaneously, with the cell kept undestroyed.

Furthermore, the measurement results of a cell-surface molecule, an intracellular molecule, a cell secretion, etc. of the cell can be analyzed integrally.

The effects described herein are not necessarily limitative ones, and there may be any of the effects described in the present disclosure.

BRIEF DESCRIPTION OF DRAWINGS

FIG. 1 is a diagram showing a light absorption pattern of a methoxynitrobenzyl.

FIG. 2 is a diagram schematically showing the binding of a single cell to a first molecule and a second molecule according to an embodiment of the present technology.

FIG. 3 is a diagram schematically showing a situation in which different specifically bound molecules are spotted in a well according to an embodiment of the present technology.

FIG. 4 is vertical cross-sectional views showing configurations of wells according to an embodiment of the present technology.

FIG. 5A to FIG. 5C are vertical cross-sectional views of wells belonging to a first to a third space according to an embodiment of the present technology.

FIG. 6A to FIG. 6C are diagrams schematically showing the release of cells by light irradiation from below the well according to an embodiment of the present technology.

FIG. 7 is a drawing-substitute photograph imaging the spots of trapped cells according to an embodiment of the present technology.

FIG. 8 is a block diagram showing the configuration of an apparatus for cell analysis according to an embodiment of the present technology.

FIG. 9 is a diagram showing an overview of a chip for cell analysis using the first space according to an embodiment of the present technology.

FIG. 10 is a flow chart showing a method for analyzing a cell using the first space according to an embodiment of the present technology.

FIG. 11 is a flow chart showing a method for analyzing a cell using the first space according to an embodiment of the present technology.

FIG. 12 is a diagram showing an overview of a chip for cell analysis using the first and second spaces according to an embodiment of the present technology.

FIG. 13 is a flow chart showing a method for analyzing a cell using the first and second spaces according to an embodiment of the present technology.

FIG. 14 is a flow chart showing a method for analyzing a cell using the first and second spaces according to an embodiment of the present technology.

FIG. 15 is a flow chart showing a method for analyzing a cell using the first and second spaces according to an embodiment of the present technology.

FIG. 16 is a flow chart showing a method for analyzing a cell using the first and second spaces according to an embodiment of the present technology.

FIG. 17 is a flow chart showing a method for analyzing a cell using the first and second spaces according to an embodiment of the present technology.

FIG. 18 is a flow chart showing a method for analyzing a cell using the first and second spaces according to an embodiment of the present technology.

FIG. 19 is a diagram showing an overview of a chip for cell analysis using the first to third spaces according to an embodiment of the present technology.

FIG. 20 is a flow chart showing a method for analyzing a cell using the first to third spaces according to an embodiment of the present technology.

FIG. 21 is a diagram showing an overview of a chip for cell analysis using the first to third spaces according to an embodiment of the present technology.

DESCRIPTION OF EMBODIMENTS

Hereinbelow, preferred embodiments of the present technology are described. The embodiments described below are typical embodiments of the present technology, and the scope of the present technology should not be construed as being limited by them. The description is given in the following order.
1. Method for analyzing a cell
(1) Step (A)
(2) Step (B)
(3) Step (C)
(4) Step (D)
(5) Step (E)
(6) Step (F)
(7) Step (G)
(8) Step (H)
(9) Integration of data obtained from the cell
2. Chip for cell analysis
3. Reagent for cell analysis
4. Kit for cell analysis
5. Apparatus for cell analysis 6. Embodiments
(1) Embodiment 1
(2) Embodiment 2
(3) Embodiment 3
(4) Embodiment 4
(5) Embodiment 5
(6) Embodiment 6
(7) Embodiment 7
(8) Embodiment 8

1. Method for Analyzing a Cell

An embodiment of the present technology includes the following:

(A) trapping a cell by means of a first molecule capable of binding to the cell, (B) binding, to a cell-surface molecule of the cell, a second molecule in which a binding portion capable of binding specifically to the cell-surface molecule, an identifying portion, and a labeling portion are linked, (C) detaching the binding portion, and the identifying portion and the labeling portion of the second molecule from each other, (D) binding, out of the identifying portion and the labeling portion detached, the identifying portion specifically to an identifying portion recognizing molecule, and (E) detecting the labeling portion out of the identifying portion and the labeling portion bound to the identifying portion recognizing molecule.

Further, identifying and/or quantifying the cell-surface molecule specifically bound to the second molecule from the detection result of the labeling portion obtained in the (E) may be included as (F).

An embodiment of the present technology may further include the following:

(G) identifying and/or quantifying a cell secretion from the cell, and/or (H) acquiring a nucleic acid from the cell and analyzing the nucleic acid.

The order in which the steps mentioned above are performed is not limited to the order of from the (A) to the (H), and may be altered. For example, the cell may be trapped after the second molecule is bound to a cell-surface molecule. In this case, the sequence may be performed in the order of from the (B) to the (A). Alternatively, in the case where a cell secretion is measured and then a cell-surface molecule is measured, the sequence may be performed in the order of from the (A) through the (G) to the (B).

(1) Step (A)

In the (A), a cell is trapped by the first molecule capable of binding to the cell.

The type of the cell to be trapped is not particularly limited, and any cell, such as an animal cell, a plant cell, or fungi, may be the object. For example, in the case of an animal cell, a cell in the blood, a cell taken from a living tissue, a cultured cell, etc. are given. Either of an adherent cell and a non-adherent cell is possible.

In an embodiment of the present technology, for example, what is called single cell trapping in which one cell is trapped into one well is performed. Hence, when cells have formed a clump of cells, it is preferable to disperse the cells into single cells by a known cell dispersion method, such as trypsin treatment, to prepare a cell suspension. Alternatively, a plurality of cells of the same type may be trapped simultaneously.

The first molecule that traps a cell is immobilized in the well (a first space). The well is not particularly limited; for example, a well in a flat-bottomed, V-shaped-bottomed, U-shaped-bottomed, plate-like, bead-like, membrane-like, or net-like configuration, etc. may be used. In an embodiment of the present technology, a configuration having a recess is preferable in view of the case of forming a flow path described later between wells.

In one well, one cell may be trapped, or a plurality of cells of the same type may be trapped.

In the case where one cell is trapped in one well, it is preferable that the first molecule be immobilized in the well so as to have a diameter size equal to or less than the diameter size of the one cell to be trapped. Cells can be trapped one by one regardless of the size of the cell.

The size of the well and the width of the flow path described later may be adjusted so that cells flow one by one like in flow cytometry and are trapped into wells one by one. Cells can be passed by, for example, a buffer, a cleaning liquid, or the like without using a sheath liquid used in flow cytometry.

It is possible for there to be a plurality of wells. In the case where wells are arranged in a row, a link is made between wells by a flow path, for example. A cell suspension may be passed from the side of the well at one end, and one cell may be trapped into one well and the untrapped cells may be passed from the well to the next well. After a cell is trapped in each well, isolation may be made by a valve provided at the flow path or the like.

Alternatively, one cell may be introduced into the recess of the well by a cell sorter.

The structure of the first molecule includes a portion capable of binding to a cell. As the portion capable of binding to a cell, for example, an oleyl group, an antibody, an aptamer, or a molecular recognition polymer may be used.

The oleyl group is hydrophobic, and adheres to a cell surface floating. The oleyl group may be provided with, for example, a spacer such as PEG, and an NHS group (N-hydroxysuccinimide group) may be contained in a terminal of the spacer; thus, the first molecule may be formed. The first molecule may be immobilized in a well coated with, for example, a collagen or the like.

In the case of the antibody, an antibody corresponding to, as the antigen, a cell-surface molecule present on the cell desired to be trapped may be used. The antibody may be immobilized in the well in a covalent bonding-like manner.

In the case of the aptamer, a nucleic acid molecule or a peptide that binds specifically to a surface molecule present on the cell desired to be trapped may be used.

In the case of the molecular recognition polymer, the cell-surface molecule of the objective can be trapped with high selectivity even in the presence of a compound having physical and chemical properties similar to those of the cell-surface molecule of the objective.

The first molecule may have a structure in which a stimulus-degradable linker is interposed between the portion capable of binding to the cell and the well at which the first molecule is immobilized.

In the case where a linker is interposed, when it is desired to recover the cell after various measurements of a cell-surface molecule, a cell secretion, etc., the cell can be recovered with good efficiency. After the recovery, the cell remains alive, and can therefore be cultured or destroyed to perform the measurement, analysis, etc. of an intracellular molecule.

The stimulus-degradable linker is a linking molecular unit that is degraded by a specific stimulus from the outside. For example, a linker that is degraded by light of a specific wavelength, a linker that is degraded by an enzyme, a linker that is degraded by temperature, and the like are given.

The stimulus-degradable linker used in an embodiment of the present technology is not particularly limited, but it is preferable to use a photodegradable linker in terms of preventing the cell from being destroyed or influenced.

The photodegradable linker is a molecular unit having a structure that is degraded by a specific wavelength, and the wavelength at which the photodegradable linker is degraded almost coincides with the absorption wavelength of the molecular unit.

For example, in the case of a methoxynitrobenzyl group used as the photodegradable linker, an absorption pattern like that shown by the solid line of FIG. 1 (before irradiation) is exhibited. Assuming that the absorption at 346 nm is 1, an absorption of 0.89 is exhibited at 364 nm, 0.15 is at 406 nm, and 0.007 is at 487 nm. That is, the methoxynitrobenzyl group has the characteristics that, when a light source of 365 nm is used, the efficiency of degradation of the photodegradable linker is good; and when a light source of 488 nm is used, the photodegradable linker is hardly degraded.

As other photodegradable linkers, for example, the following may be given: a nitrobenzyl group (JP 2010-260831A), a parahydroxyphenacyl group (Tetrahedron Letters, 1962, vol. 1, p. 1), a 7-nitroindoline group (Journal of the American Chemical Society, 1976, vol. 98, p. 843), a 2-(2-nitrophenyl)ethyl group (Tetrahedron Letters, 1997, vol. 53, p. 4247), a (coumarin-4-yl)methyl group (Journal of the American Chemical Society, 1984, vol. 106, p. 6860), etc.

The wavelength of the light applied to the photodegradable linker may be a wavelength corresponding to each photodegradable linker. For example, a wavelength near 330 to 450 nm is given. It is preferable to perform irradiation at, for example, 30 mW/cm^2 multiplied by 100 sec., i.e. 3 J/cm^2, which does not damage the cell. In particular, wavelengths of 300 nm or less may damage the cell, and are therefore preferably not be used.

With regard to the cytotoxicity caused by UV, depending on the type of the cell, it is said that the DNA is damaged and the cell growth is inhibited at 500 J/cm^2 (Callegari, A. J. & Kelly, T. J. Shedding light on the DNA damage checkpoint. Cell Cycle 6, 660-6 (2007)). Further, there is a report that cytotoxicity does not occur at 42 J/cm^2 (Masato T, et al., Optical cell separation from three-dimensional environment in photodegradable hydrogels for pure culture techniques, Scientific Reports 4, Article Number. 4793(2014)).

(2) Step (B)

In the (B), the second molecule in which the binding portion capable of binding specifically to a cell-surface molecule, the identifying portion, and the labeling portion are linked is bound to the cell-surface molecule of the cell.

Various cell-surface molecules are present on the cell trapped in the (A). The cell-surface molecule is a sugar strand, a protein, a lipid, or the like. As specific cell-surface molecules, for example, a CD antigen, various families of cell-adherent molecules, a cell-surface receptor, etc. are given.

The second molecule includes the binding portion capable of binding specifically to a cell-surface molecule, the identifying portion, and the labeling portion.

For the binding portion capable of binding specifically to a cell-surface molecule, for example, the whole of an antibody, a variable region portion of an antibody, an aptamer, or a molecular recognition polymer may be used.

The binding reaction between the cell-surface molecule and the second molecule, the binding reaction to the first molecule of the (A), etc. are not particularly limited; the reaction may be performed for a certain period of time while the whole well is cooled at, for example, 4° C. or is warmed at approximately 37° C., which is near the body temperature of animals.

The identifying portion is linked to the binding portion. For the identifying portion, for example, various proteins and peptides, a nucleic acid (a DNA strand or an RNA strand) fragment, etc. may be used. In an embodiment of the present technology, although there are no particular limitations, a nucleic acid fragment is preferably used. The size of the nucleic acid fragment is not particularly limited; for example, a DNA fragment composed of 3 to 100 nucleic acid nucleotide units may be used.

A DNA fragment is preferable because various sequences can be created in accordance with the combination of A, T, G, and C of the nucleic acid.

The antibody that binds to a cell-surface molecule (antigen) is said to have approximately 350 types, and DNA sequences corresponding to all of the antibodies can be created when the label is created by a DNA sequence of an oligo-level length (approximately 20 bases or less).

The labeling portion is linked to the identifying portion linked to the binding portion. The label used for the labeling portion may be a known one; for example, a fluorescent molecule, an RI label, a hapten, an affinity tag, an enzyme, a metal, etc. are given.

In the case where a fluorescent molecule is used for the labeling portion, the number of colors may be one or may be two or more. In the case where a metal is used, the detection can be made by TOF-MS.

The labeling is not limited to fluorescent labeling etc., and a method in which optical detection can be made by making luminescence, color development, or the like on the spot, without diffusion, may be used. For example, electrochemiluminescence is possible when a ruthenium complex is used as the label and an electrode is provided on a substrate surface.

It is also possible to bind horseradish peroxidase (HRP) or a luciferase to the identifying portion, add a chemiluminescent substrate (luminol, lucigenin, an adamantyl dioxetane derivative, etc.) or a bioluminescent substrate (a luciferin, a bacterial luciferase, coelenterazine, etc.), and detect the luminescence intensity.

In electrochemiluminescence, chemiluminescence, and bioluminescence, the signal can be amplified and thus high-sensitivity detection can be made.

Further, the detection may be performed using an intercalator such as SYBR Green I.

A stimulus-degradable linker may be interposed between the binding portion, and the identifying portion and the labeling portion; as the stimulus-degradable linker, the photodegradable linker described above may be used, for example.

Further, the fact that the wavelength suitable for photodegradation varies depending on the type of the photodegradable linker may be utilized. For example, linkers that are degraded by different wavelengths are used for second molecules that bind to different cell-surface molecules. Then, light of a wavelength suitable for any of the photodegradable linkers may be applied; thus, a portion including the identifying portion and the labeling portion of the desired type based on the linker can be isolated from the second molecule bound to the target cell-surface molecule.

In FIG. 2, a schematic diagram in which a single cell 22 is trapped by a first molecule 21 immobilized in a well 26 of a first space and a second molecule 24 is bound to a cell-surface molecule 23 of the trapped single cell is shown. This is an example in which a stimulus-degradable linker 25 is included in the first molecule 21 and the second molecule 24 and a metal 27 or a nucleic acid fragment 28 is used as the identifying portion and/or the labeling portion of the second molecule.

Also an example in which a typical fluorescently labeled substance 29 in related art is used is shown.

(3) Step (C)

In the (C), the binding portion, and the identifying portion and the labeling portion of the second molecule are detached from each other.

The detachment is performed by stimulating the stimulus-degradable linker. In the case of a photodegradable linker, the well of the trapped cell may be irradiated such that the photodegradable linker of the second molecule is included in the area of light irradiation.

The second molecule degraded by the light irradiation is separated into the binding portion, and the identifying portion and the labeling portion. The binding portion remains bound to the cell-surface molecule of the trapped cell. On the other hand, the identifying portion and the labeling portion detached and isolated may be passed on a solution basis or may be passed by a buffer liquid or the like, and can be transferred to the next well (a second space etc.).

(4) Step (D)

In the (D), out of the identifying portion and the labeling portion isolated, the identifying portion is bound specifically to the identifying portion recognizing molecule.

The identifying portion recognizing molecule includes a recognizing molecular unit corresponding to the identifying portion used for the second molecule. For example, in the case where the identifying portion of the second molecule is a protein or a peptide, an antibody is used for the identifying portion recognizing molecule. In the case where the identifying portion of the second molecule is a nucleic acid fragment, a fragment having a nucleic acid sequence complementary to the nucleic acid fragment is used.

The identifying portion recognizing molecule may be immobilized in the well in which the first molecule is immobilized (the first space), or may be immobilized in another well (the second space etc.). A plurality of types of identifying portion recognizing molecules may be immobilized in one well. The identifying portion recognizing molecule may be immobilized in an array configuration on a type basis. For example, when fragments having nucleic acid sequences are used as the identifying portion recognizing molecule, a configuration like a DNA chip can be created.

Furthermore, the immobilization may be made while one well is divided into, for example, a region where a molecule for cell-surface molecule measurement is immobilized (a first region) and a region where a molecule for intracellular molecule measurement is immobilized (a second region). As long as the positions of spots for immobilization do not overlap, the distinction is possible on the basis of the information in which the immobilized molecule and the spot position are correlated.

An example is shown in FIG. 3. On the left side of a well 31, spots 34 of identifying portion recognizing molecules for cell-surface molecule measurement 32 are arranged in 3 longitudinal rows and 6 transverse rows. On the right side, spots 34 of identifying portion recognizing molecules for intracellular molecule measurement 33 are arranged in 3 longitudinal rows and 6 transverse rows. When 350 types of molecules are to be measured, 350 spots are prepared and different molecules are immobilized individually to them. The spot size may be not less than the surface area of the cell.

The configuration of the well is not particularly limited, and may be selected in accordance with the molecule to be immobilized etc. For example, the molecule may be immobilized to a flat surface of the well (the upper portion of FIG. 4), may be immobilized to a convex portion of the well (the middle portion of FIG. 4), or may be immobilized to a concave portion of the well (the lower portion of FIG. 4).

Out of the identifying portion and the labeling portion detached in the (C), the identifying portion binds specifically to the identifying portion recognizing molecule for cell-surface molecule measurement thus immobilized in the well.

For example, in the case where the identifying portion is a nucleic acid fragment, the identifying portion binds to a spot to which an identifying portion recognizing molecule (a DNA strand or the like) having a sequence complementary to the nucleic acid fragment is immobilized.

In the case where the identifying portion is a protein or a peptide, the identifying portion binds to a spot to which an identifying portion recognizing molecule (an antibody) that recognizes the protein or the peptide as the antigen is immobilized.

(5) Step (E)

In the (E), out of the identifying portion and the labeling portion bound specifically to the identifying portion recognizing molecule in the (D), the labeling portion is detected.

The labeling portion includes, as described above, a labeling molecular unit of a fluorescent molecule, an RI label, a hapten, an affinity tag, an enzyme, a metal, etc. The labeling portion is detected by a detection method corresponding to the labeling molecular unit being used. For example, in the case where a fluorescent molecule is used as the labeling portion, light of the excitation wavelength may be applied to the fluorescent molecule.

When the labeling portion is an RI label, a hapten, an affinity tag, or an enzyme, or a metal, the identification and/or quantification may be performed using radiation, an antibody for detection, or TOF-MS etc., respectively.

The combination of the molecules used for the identifying portion and the labeling portion is not particularly limited in an embodiment of the present technology. A protein, a peptide, a nucleic acid fragment, etc. as the identifying portion and a fluorescent molecule, an RI label, a hapten, an affinity tag, an enzyme, a metal, etc. as the labeling portion may be combined freely.

In an embodiment of the present technology, preferably a nucleic acid fragment as the identifying portion and a fluorescent molecule as the labeling portion may be combined, for example.

(6) Step (F)

In the (F), the cell-surface molecule bound specifically to the second molecule is identified and/or quantified from the detection result of the labeling portion obtained in the (E).

As described above, in the case where, for example, a nucleic acid fragment is used for the identifying portion, a much larger number of types of nucleic acid fragments than the number of types of cell-surface molecules that are supposed to exist today, i.e. approximately 350 types, can be prepared by combining A, T, G, and C.

As described above, as long as nucleic acid fragments complementary to more than 350 types of nucleic acid fragments are immobilized individually to different spots of the well on a type basis, the type of the nucleic acid fragment and the position of the spot are correlated, and this is grasped as position information.

The type and expression level of the cell-surface molecule are found by what spot emits what degree of fluorescence. By the development to the position information, comprehensive measurement of more than 350 types of cell-surface molecules can be made.

In the case where, in particular, the shape of the well is a flat surface, since the reacted substrate diffuses, it is presumed that spotted places will be difficult to identify when the spot positions are near. In this case, a shape that can suppress the diffusion may be employed, such as a shape in which the spot portion is recessed.

It is preferable that the identifying portion and the labeling portion that are isolated from the second molecule and are not bound to the identifying portion recognizing molecule be removed to reduce the background noise and thus high-sensitivity measurement be performed. Hence, after a certain period of reaction with the identifying portion recognizing molecule immobilized in the well, it is preferable to pass a cleaning liquid or the like in order to remove the identifying portion and the labeling portion that are isolated from the second molecule and are unbound.

(7) Step (G)

In the (G), a cell secretion from the cell is identified and/or quantified.

The trapped cell is alive even after undergoing the (A) to (F). Hence, a cell secretion can be secreted in the well while in the trapped state. Alternatively, the trapped cell may be released and put into another container to cause a cell secretion to be secreted. The cell secretion is not particularly limited in an embodiment of the present technology, and any cell secretion may be the object. As the cell secretion, for example, various hormones such as insulin and secretin, various enzymes such as pepsinogen, a cytokine, a chemokine, perforin, a granzyme, an exosome, etc. are given.

Here, at the time of causing a cell secretion to be secreted, the cell may be stimulated. A physical stimulus, a chemical stimulus, or the like may be applied to the cell. In the case of an immunocyte, it may be associated with a tumor cell.

For example, a cell secretion-stimulating substance may be applied to the cell. The cell secretion-stimulating substance varies with the type of the cell, the type of the secretion, etc.; for example, a sugar, an amino acid, a fat, an acid, and an alkali (a pH adjuster) are given.

The identification and/or quantification of the cell secretion can be performed by a commonly used method. For example, a label may be attached to an antibody corresponding to a specific cell secretion as the antigen, and after an antigen-antibody reaction, the detection and/or intensity measurement of the label may be performed.

Alternatively, in a well (a third space) adjacent to the well (the first space) in which the first molecule is immobilized, an antibody, an aptamer, a molecular recognition polymer, or the like that binds specifically to a cell secretion is immobilized in a specific place. After the immobilized antibody or the like and the cell secretion secreted from the cell are bound together, a labeled molecule (an antibody, an aptamer, a molecular recognition polymer, or the like) is introduced; thus, a sandwich immunoassay etc. can be performed. For the reaction at this time, for example, the electrochemiluminescence, chemiluminescence, bioluminescence, etc. described above may be used.

In the case where the trapped cell is released and cell secretion, the nucleic acid analysis of the cell described later, and other analyses regarding the cell are performed, the first molecule that traps the cell is preferably structured to be immobilized via a stimulus-degradable linker, as described above. At the time of releasing the cell, the cell can be easily recovered by applying a stimulus to the stimulus-degradable linker.

(8) Step (H)

In the (H), a nucleic acid is acquired from the cell and is analyzed.

Since the cell is still alive even after undergoing the (A) to (G), the cell may be destroyed and thus a nucleic acid can be acquired and analyzed.

The acquisition and analysis of a nucleic acid can be performed by a commonly used method. For example, they can be performed by a method in which a nucleic acid is extracted, purified, and amplified (the PCR method etc.) and the nucleic acid sequence is determined.

It is also possible to, after the extraction, perform up to preliminary amplification, and recover the amplified substance to determine the nucleic acid sequence with a next-generation sequencer or the like.

(9) Integration of Data Obtained from the Cell

In the (F), data of the identification and/or quantification of a cell-surface molecule present on the cell are obtained. When the data and other data regarding the cell are integrated, analysis using the same living cell becomes possible.

For example, in the (G), data of the identification and/or quantification of a secretion from the cell are obtained. When the data obtained in the (F) and the data obtained in the (G) are integrated, the relationship between the cell-surface molecule and the cell secretion of the living cell can be analyzed.

Furthermore, in the (H), data of a nucleic acid of the cell can be acquired. When the data obtained in the (F) and the data obtained in the (H) are integrated, the relationship between the cell-surface molecule and the gene expressed in the living cell can be analyzed.

Furthermore, the data obtained in the (F), the (G), and the (H) may be integrated. Thereby, the relationships between the cell-surface molecule, the cell secretion, and the gene in the living cell can be made clear.

According to an embodiment of the present technology, with the cell kept undestroyed, cell-surface molecules thereof (antigens etc.) can be measured comprehensively, and also molecules that the cell has secreted due to a stimulus or the like can be measured comprehensively, by the above steps. When the measurement results in the second space and the third space are compared, the cell surface information and the cell secretion information (cell response information) can be integrated reliably at a level of what is called a single cell.

2. Chip for Cell Analysis

By a chip for cell analysis of an embodiment of the present technology, all the steps from the trapping of a cell from a cell suspension up to various measurements can be performed in the chip.

In the chip for cell analysis of an embodiment of the present technology, a first region, a second region, and a detection region are included.

The first molecule capable of binding to a cell is immobilized in the first region.

A molecule capable of binding specifically to the second molecule in which the binding portion capable of binding specifically to the cell, the identifying portion, and the labeling portion are linked is immobilized in the second region.

A molecule that binds specifically to the identifying portion, for example, is immobilized in the detection region so that the labeling portion can be detected.

The first region, the second region, and the detection region may be present in one well or may be present individually in different wells, or a plurality of regions may be present in one well and other regions may be present in other wells.

A link may be made between wells by a flow path, and the flow path may be provided with a valve.

For example, the chip for cell analysis of an embodiment of the present technology includes a plurality of wells belonging to the first space, and the wells of the first space are linked by a flow path. In the case where the wells are arranged in one row, they are linked in one row by a flow path. Although it is possible for a sample such as a cell suspension, a reagent, a cleaning liquid, etc. to be put into each well, they may be put into the well at one end and passed toward the well at the other end because the wells are linked by the flow path. The passing may be performed at a low rate of several tens of centimeters per second or less and low pressure, for example.

The flow path is provided with a valve. The valve is in a openable and closable structure; for example, it can be closed when the sample and the reagent are reacted in each well, and can be opened when the sample and the reagent are passed to another well.

In the well belonging to the first space, the first molecule is immobilized so that one cell is trapped into one well. For example, the first molecule may be immobilized in the well so as to have a diameter size equal to or less than the diameter size of one cell to be trapped.

The first molecule is preferably immobilized in the well via a stimulus-degradable linker.

The chip for cell analysis may further include a well belonging to another space. For example, the chip for cell analysis may include a well belonging to the second space, the third space, etc. on the same plate as the first space. Thereby, a cell-surface molecule, an intracellular molecule, a cell secretion, etc. can be measured on the same plate. Furthermore, since there are a plurality of wells, it becomes possible to give specific biological conditions such as stimulus application to the cell etc., and it also becomes possible to measure and analyze the cell over time.

Similarly to the wells belonging to the first space, the wells belonging to the second space may be arranged in one row and linked in one row by a flow path, for example. This similarly applies to the third space etc.

In the case where the wells belonging to the first space and the wells belonging to the second space are arranged parallel in two rows, the wells belonging to the first space and the wells belonging to the second space arranged adjacent thereto may be linked by a flow path. The flow path may be provided with a valve.

In the well of the second space, for example, the identifying portion recognizing molecule described above may be immobilized.

When using the chip for analysis of such a structure, first, a cell is trapped by the first molecule immobilized in the first space. Next, the second molecule including the binding portion capable of binding specifically to a cell-surface molecule of the cell is reacted. In this time, the valve of the flow path between the well of the first space and the well of the second space is closed.

A stimulus is applied to the second molecule bound to the cell-surface molecule of the cell trapped in the well of the first space to degrade the stimulus-degradable linker, and thus the identifying portion and the labeling portion of the second molecule are isolated.

Next, in order to transfer the identifying portion and the labeling portion isolated to the well of the second space, the valve of the flow path between the well of the first space and the well of the second space is opened. The liquid existing in the well of the first space and containing the identifying portion and the labeling portion flows into the well of the second space. After the liquid has flowed in, the valve is closed.

In the well of the second space, the identifying portion out of the identifying portion and the labeling portion isolated from the second molecule and the identifying portion recognizing molecule immobilized in the well of the second space are reacted together.

In the case where wells belonging to the third space are further arranged in addition to those belonging to the second space, for example, the wells belonging to the first space may be arranged in one longitudinal row on the center, the wells belonging to the second space may be arranged in one longitudinal row on the right side of the wells belonging to the first space, and the wells belonging to the third space may be arranged in one longitudinal row on the left side of the wells belonging to the first space.

A link may be made also between wells belonging to the third space by a flow path, and a valve may be provided. The wells belonging to the third space and the wells belonging to the first space immediately on the right side thereof may be linked by a flow path, and a valve may be provided.

In the well belonging to the first space, the trapped cell may be dissolved, and the extraction, purification, preliminary amplification, amplification, etc. of a nucleic acid may be performed.

Here, cross-sectional views of wells belonging to the first, second, and third spaces are shown in FIG. 5. In FIG. 5, it is assumed that the left side is the third space, the center is the first space, and the right side is the second space. FIG. 5A shows a situation in which cells are allowed to flow into the well belonging to the first space ((1) of FIG. 5A), a single cell is trapped, and the second molecule is bound to a cell-surface molecule of the single cell. At this time, the valve of the flow path making a link from the well belonging to the first space to the well belonging to the second space is closed. Also the valve of the flow path making a link from the well belonging to the first space to the well belonging to the third space is closed.

In FIG. 5B, in the well belonging to the first space on the center, the stimulus-degradable linker of the second molecule is degraded, and thus the identifying portion and the labeling portion are isolated. The valve of the flow path making a link from the well belonging to the first space to the well belonging to the second space on the right side thereof is opened, and the identifying portion and the labeling portion isolated flow into the well belonging to the second space ((2) of FIG. 5B). In the well belonging to the second space, the identifying portion recognizing molecule is immobilized, and the identifying portion that binds specifically to the identifying portion recognizing molecule binds to it; then, measurement is performed.

In FIG. 5C, the single cell trapped in the well belonging to the first space on the center is dissolved, and the extraction etc. of an intracellular molecule (e.g. a nucleic acid) are performed. The valve of the flow path to the well belonging to the third space on the left side is opened, and the nucleic acid flows into the well belonging to the third space ((3) of FIG. 5C). In the well belonging to the third space, an intracellular molecule recognizing molecule is immobilized, and binds specifically to the nucleic acid; then, measurement is performed.

When the cell is not dissolved, in-situ hybridization, in-situ PCR, in-situ sequencing, etc. may be performed. After cell membrane permeation treatment, the intracellular molecule may be stained and observed.

Alternatively, without performing the extraction etc. of a nucleic acid in the well belonging to the first space, a stimulus may be applied to the first molecule to degrade the stimulus-degradable linker to release the cell. The released cell may pass through the flow path and go into the well belonging to the third space, and another analysis, culture, etc. can be performed in the well. The released cell may be transferred to a fourth space, another container, etc.

In the wells belonging to the first, second, third, and other spaces, any molecule may be immobilized other than the first molecule and the second molecule that is the identifying portion recognizing molecule described above. For example, a molecule that recognizes a cell secretion, an antibody that recognizes an intracellular molecule of the cell, a molecule that has a sequence complementary to the sequence of a nucleic acid of the cell, etc. are given.

When, for example, it is desired to measure the information of a cell-surface molecule and an intracellular molecule, as shown in FIG. 3 described above, a nucleic acid fragment having a sequence complementary to the nucleic acid fragment bound to the cell-surface molecule may be immobilized in the well belonging to the second space, and a molecule that binds specifically to the intracellular molecule or a molecule that binds complementarily to the intracellular molecule may be immobilized in the well belonging to the third space.

As another pattern, the wells of the first, second, third, and other spaces may be divided into a plurality of regions, and a different molecule may be immobilized in each region.

For example, one well of the first space is divided into the first region and the second region; and the first molecule capable of binding to a surface molecule is immobilized in the first region, and the second molecule in which the binding portion capable of binding specifically to a cell-surface molecule, the identifying portion, and the labeling portion are linked and/or a molecule capable of binding specifically to a cell secretion from the cell is immobilized in the second region.

As still another pattern, in the well belonging to the second space, a nucleic acid fragment complementary to the identifying portion included in the second molecule may be immobilized in the first region, and a nucleic acid fragment that binds specifically to an intracellular molecule may be immobilized in the second region; and in the entire well belonging to the third space, a molecule that binds specifically to a cell secretion may be immobilized.

In this case, first, the nucleic acid fragment complementary to the identifying portion included in the second molecule is isolated by applying a stimulus to the stimulus-degradable linker, and is sent to the well belonging to the second space. Subsequently, a cell secretion secreted by the stimulation or the like of the cell trapped in the well belonging to the first space is sent to the well belonging to the third space. After that, the cell is dissolved in the well belonging to the first space, and an intracellular molecule is sent to the well belonging to the second space. After a certain period of reaction is finished, in order to remove the unbound molecules, the well belonging to the second space is cleaned by opening the valve, and next the well belonging to the third space is cleaned by opening the valve. After that, the position and amount of luminescence are measured by adding a reactive substrate or the like. In the case of measuring an intracellular DNA or mRNA, preliminary amplification, if necessary, is performed in the well belonging to the first space. After that, the amplified substance may be transferred to the well belonging to the second space.

It is also possible to, after preliminary amplification in the well belonging to the first space, recover the solution and perform measurement in another apparatus such as a sequencer. In the case where the cell is not dissolved in the well belonging to the first space, the stimulus-degradable linker of the first molecule trapping the cell may be degraded to recover the cell.

A photodegradable linker may be used as the stimulus-degradable linker as described above. In this case, as the photodegradable linker of the first molecule, a linker that degrades at a wavelength different from the wavelength at which the photodegradable linker used for the second molecule that binds to a cell-surface molecule degrades may be used. For example, the photodegradable linker used for the second molecule is degraded at 365 nm, and the photodegradable linker used for the first molecule is degraded at 700 nm.

To degrade the photodegradable linker, a situation in which light of a specific wavelength can be applied from below the well belonging to the first space is created. To shorten the time, a light source may be placed below each well. However, the configuration is not limited thereto, and scanning may be used. In the case of a light source allowing irradiation for a certain area, shutters capable of opening and closing in a minute range may be arranged in the area. Furthermore, a digital micro-device may be used to perform irradiation on only a specific area.

In FIG. 6, a schematic diagram in which light is applied from below the well belonging to the first space to degrade the photodegradable linker to release the cell is shown.

FIG. 6A shows a situation in which first molecules are immobilized in the well belonging to the first space. A photodegradable linker is included in the first molecule. FIG. 6B shows a situation in which cells are allowed to flow into the well belonging to the first space, cells are trapped by the first molecules, and second molecules are bound specifically to cell-surface molecules. FIG. 6C shows a situation in which, for the portion irradiated with light 61 from below the well belonging to the first space, the photodegradable linker is degraded, and thus the trapped cells are released.

The light irradiation may be performed with, for example, 1 J/cm$^2$ (in the case of 100 mW/cm$^2$, 10 s).

When the timing of light irradiation is varied, the photodegradable linkers of the first molecule and the second molecule can be degraded with a time difference, and therefore also the release can be made with a time difference.

In FIG. 7, an image diagram in which cells are trapped by immobilized first molecules is shown. According to an embodiment of the present technology, cells can be trapped by a single layer with high density. Thus, the detection and observation of a cell-surface molecule, an extracellular secreted substance, and an intracellular molecule may be performed while a plurality of cells of the same type are trapped in one well.

As the plurality of cells of the same type, cultured cells from the same cell line, a cell population of which the cells are regarded as identical by flow cytometry (a cell group displayed in the same gate region by flow cytometry), etc. are given.

For the wells belonging to the second and third spaces, a CMOS or the like capable of photographing a certain area collectively may be placed below the well, and thereby the wells belonging to the second and third spaces can be scanned and photographed. When a certain sensitivity is desired, the exposure time may be extended. A plurality of molecules of the detection object can be detected collectively, and also imaging analysis becomes possible. As the apparatus, for example, the sCMOS of IN Cell Analyzer 6000 (GE Healthcare) is given. By using this, one well (approximately 0.33 cm$^2$) of a 96-well plate can be photographed at one time. The entire 96-well plate (approximately 31.68 cm$^2$) can be photographed in approximately 4 minutes.

3. Reagent for Cell Analysis

A reagent of an embodiment of the present technology is a reagent used for the method for analyzing a cell described above, and contains a molecule including a binding portion capable of binding specifically to a molecule selected from the group consisting of a cell-surface molecule, an intracellular molecule, and a cell secretion and a labeling portion. For example, a reagent containing the second molecule, a reagent containing a molecule that binds specifically to a cell secretion and is labeled, a reagent containing a molecule that binds specifically to an intracellular molecule and is labeled, and the like are given. For the molecule contained in the reagent, one type of molecule or a plurality of types of molecules may be contained in one reagent.

4. Kit for Cell Analysis

A kit for cell analysis of an embodiment of the present technology may include the chip for cell analysis mentioned above and at least one reagent or any combination of two or more reagents selected from the group consisting of the reagent for cell analysis mentioned above, a reagent that detects the labeling portion, and a reagent containing a substance that stimulates cell secretion.

5. Apparatus for Cell Analysis

In FIG. 8, an example of the apparatus for cell analysis used in an embodiment of the present technology is shown.

The apparatus includes an insertion unit 84, a fluid control unit 81, a light irradiation unit 83, a detection unit 85, a memory unit 86, and a processing unit 82.

The insertion unit 84 has the function of inserting the chip for cell analysis mentioned above into the apparatus for cell analysis and setting the chip for cell analysis.

The fluid control unit 81 has the function of introducing a liquid containing cells, a liquid containing a cell secretion, a reagent, a cleaning liquid, etc. into a well, the function of passing these liquids to another well via a flow path, the function of discharging unnecessary liquids, etc.

The light irradiation unit 83 includes a light source that irradiates the well with light of a wavelength suitable to degrade the photodegradable linker that is included in the first molecule immobilized in the well of the chip for cell analysis described above or in the second molecule.

The detection unit 85 has the function of detecting and/or quantifying the cell introduced and trapped in the chip for cell analysis mentioned above, a cell secretion, a cell-surface molecule, etc. by the measurement of the label or the like.

In the memory unit 86, the operation of the insertion unit 84, the fluid control unit 81, the light irradiation unit 83, and the detection unit 85 may be stored, and in addition, data obtained in the detection unit etc. may be stored.

The processing unit 82 performs sequence processing mutually with each unit on the basis of the memory of the memory unit 86, and executes the operation of the insertion unit 84, the fluid control unit 81, the light irradiation unit 83, and the detection unit 85.

An example of the operation of the apparatus is as follows.

First, the chip for cell analysis mentioned above is installed into the apparatus used in an embodiment of the present technology by the insertion unit 84. Next, the fluid control unit 81 is put into operation by the processing unit 82, and a liquid containing cells is introduced into the well at an end of the first space. Next, the fluid control unit 81 opens the valve provided at the flow path between wells to pass the liquid containing cells. One cell is trapped by the first molecule immobilized in each well, and the untrapped cells are removed by passing a cleaning liquid or the like.

The fluid control unit 81 is put into operation so that a liquid containing second molecules that bind specifically to a cell-surface molecule is introduced into the well at the end of the first space, and the liquid containing second molecules is passed to the well on the downstream side via the flow path. A second molecule binds to the cell trapped by the first molecule, and the unbound second molecules are removed by passing a cleaning liquid or the like by the fluid control unit 81.

The second molecule bound specifically to a cell-surface molecule is irradiated with light from the light irradiation unit 83 to cut the photodegradable linker of the second molecule, and thus the identifying portion and the labeling portion of the second molecule are isolated. The position, timing, wavelength, intensity, time, etc. of the light irradiation are stored as a program in the memory unit 86, and are implemented by driving the light irradiation unit 83 via the processing unit 82.

Next, the fluid control unit 81 is put into operation to open the valve provided between the well of the first space and the well of the second space, and the liquid containing the identifying portion and the labeling portion isolated is passed from the well of the first space to the well of the second space.

In the well of the second space, a molecule that binds specifically to the identifying portion is immobilized, and the identifying portion out of the identifying portion and the labeling portion passed binds to the immobilized molecule. The fluid control unit 81 is put into operation to introduce a cleaning liquid or the like into the well at an end of the second space, and the identifying portion and the labeling portion that have not been bound in the well of the second space are removed via the flow path.

The labeling portion out of the identifying portion and the labeling portion bound in the well of the second space is detected and/or quantified by the detection unit 85. The data obtained here may be stored in the memory unit 86.

As the detection method, a known method such as detection by applying light of a wavelength suitable for the label may be used when the label is a fluorescent label. Also the light irradiation at this time may be performed by the light irradiation unit 83.

On the other hand, for the cell trapped in the well of the first space, a cell secretion may be further detected and/or quantified. The data of the cell secretion may be stored in the memory unit 86.

Alternatively, the first molecule may be irradiated with light from the light irradiation unit 83 to release the cell. The released cell may be used for the measurement of an intracellular molecule, or may be used for culture, for example.

6. Embodiments

Embodiments of the present technology will now be specifically described with reference to the drawings.

(1) Embodiment 1

A case of using only the first space will now be described. In this case, for example, the measurement of a cell secretion, the measurement of a cell-surface molecule, the preliminary amplification of an intracellular mRNA, or cell recovery can be performed, and the conditions of the cell can be found.

An overview of a chip for cell analysis is shown in FIG. 9.

In FIG. 9, four wells W1 to W4 are arranged longitudinally. In each well, an antibody that binds to a specific cell-surface molecule is immobilized via a photodegradable linker (the immobilization of the first molecule). Further, an antibody that binds to another cell-surface molecule and an antibody that binds to a cell secretion are immobilized in each well. The wells are linked by a flow path 16, and valves 3 to 5 are provided individually between adjacent ones of the wells.

The well W1 may be used as an inlet of cells, cleaning liquids, etc., and the trapped cell may be used as a control for measurement etc.

In FIG. 10, a flow of Embodiment 1 after the chip for cell analysis is inserted into the apparatus for cell analysis is shown. A description will now be given with reference to FIG. 9, FIG. 10, and FIG. 8.

First, the second molecule in which the binding portion capable of binding specifically to a cell-surface molecule, the identifying portion, and the labeling portion are linked is bound to the cell-surface molecule of the cell, and thus the cell-surface is labeled (S971). A photodegradable linker is included in the second molecule. When labels individually corresponding to various cell-surface molecules are bound, the types, the amounts of presence, etc. of the cell-surface molecules can be made clear by measuring the presence or absence and the intensity of the labels afterward.

Next, on the basis of the memory based on the memory unit 86, the fluid control unit 81 is put into operation by the processing unit 82, and a liquid containing cells labeled by the second molecule is introduced into the well W1. At this time, the valves 3 to 4 are opened so that the labeled cells flow in the direction from the arrow of FIG. 9 to the wells W2 to W4 sequentially. While the cells flow through the wells W1 to W4, one cell is trapped by the first molecule that is capable of binding to the cell and is immobilized in the well (S972). The untrapped cells are washed to the downstream side of W4 by the fluid control unit 81 and are removed (S973). At this time, a cleaning liquid or the like may be used in order to wash the cells away.

Next, the valves 3 to 5 are closed by the fluid control unit 81, and by the light irradiation unit 83, the cell-surface label is isolated, that is, the binding portion, and the identifying portion and the labeling portion of the second molecule are detached and isolated from each other (S982). The identifying portion and the labeling portion isolated are trapped at the bottom surface of each of the wells W1 to W4, and the detection and measurement of the labeling portion are performed by the detection unit 85 (S983). By the measurement, what kind of cell-surface molecule is present on one cell to what degree can be made clear. The measurement results may be stored as data in the memory unit 86.

On the other hand, a cell secretion secreted to the outside of the cell is trapped by the antibody or the like immobilized at the bottom surface of each well, and is identified and/or quantified by the detection unit 85 (S984). Thereby, what kind of cell secretion has been secreted from one cell to what degree can be made clear. The measurement results may be stored as data in the memory unit 86.

After that, a nucleic acid is acquired from the cell and is analyzed. In the case where a DNA or an mRNA of an intracellular molecule is preliminarily amplified, with the valves 3 to 5 kept closed, preliminary amplification by cell dissolution, the multi-displacement amplification method, etc. is performed (S980), and the solution is recovered. The recovered solution may be used for the analysis of the DNA or the mRNA, etc.

It is also possible to perform steps (S1071 to S1084) similar to S971 to S984 of FIG. 10 and then recover the cell. The photodegradable linker of the first molecule is degraded by light irradiation, and thus the cell is isolated and recovered (S1081). The recovered cell may be used for culture etc.

(2) Embodiment 2

A case of using the first and second spaces will now be described. In this case, for example, the measurement of a cell secretion, the measurement of a cell-surface molecule, the preliminary amplification of an intracellular mRNA, or cell recovery can be performed. In the second space, a cell secretion secreted to the outside of the cell and a cell-surface molecule label can be measured.

Also environment control by cell secretion stimulation or the like may be performed, and also the change in conditions of the cell may be measured.

An overview of a chip for cell analysis is shown in FIG. 12.

Four wells W1 to W4 are arranged longitudinally in a first space 11. An antibody that binds to a cell-surface molecule is immobilized in the wells W1 to W4 via a photodegradable linker.

In a second space 12 on the right side of the first space 11, four wells W5 to W8 are arranged longitudinally. An antibody that binds to a cell secretion and the identifying portion recognizing molecule are immobilized in the wells W5 to W8. The wells W1 to W4 and the wells W5 to W8 are linked individually by longitudinal flow paths. Also the wells of the first space and the second space are linked transversely by the flow path 16 except for the wells W1 and W5 at the upper end. The flow path is provided with valves 1, 3, 4, and 5.

Although it is possible for the wells W1 and W5 to be linked, by not linking the wells W1 and W5, the well W1 can be used as an inlet of cells, cleaning liquids, etc., or the cell trapped in the well W1 can be used as a control for measurement etc.

In FIG. 13, a flow of Embodiment 2 after the chip for cell analysis is inserted into the apparatus for cell analysis is shown. A description will now be given with reference to FIG. 12, FIG. 13, and FIG. 8.

First, on the basis of the memory based on the memory unit 86, the fluid control unit 81 is put into operation by the processing unit 82 to close the valve 1 and open the valves 3 to 5, and a liquid containing cells is introduced into the well W1 at the upper end of the first space 11 and is passed from the well W1 to the well W4. During the passing, one cell is trapped into each well by the first molecule that is capable of binding to the cell and is immobilized (S1272).

The unbound cells are washed to the downstream side of the well W4 and are removed (S1273). To wash the cells away, a cleaning liquid or the like may be used.

Next, the environment of the trapped cell is controlled (S1274). For example, a cell secretion-stimulating substance that stimulates cell secretion is introduced by the fluid control unit 81. The cell secretion can be made active by the stimulating substance. At this time, the valves 3 to 5 may be opened to introduce the same stimulating substance, or the valves 3 to 5 may be closed to introduce a different stimulating substance to each well.

Only the valve 1 is opened, and the liquid containing a cell secretion secreted to the outside of the cell is transferred to the well of the second space by the fluid control unit 81 (S1275). The cell secretion of the well W2 is transferred to the well W6, the cell secretion of the well W3 is to the well W7, and the cell secretion of the well W4 is to the well W8. After the transfer, the valve 1 is closed.

The cell secretion is trapped by the antibody or the like immobilized at the bottom surface of the well of the second space, and is measured by the detection unit 85 (S1276). By the measurement, what kind of cell secretion has been secreted from one cell to what degree can be made clear. The measurement results may be stored as data in the memory unit 86.

Next, the valve 1 is closed, and a label is attached by the second molecule or the like to a cell-surface molecule of the cell that remains trapped in the well of the first space 11 (S1277). When the valves 3 to 5 are opened, a liquid containing second molecules can be passed in the direction from W1 to W4. Alternatively, all the valves may be closed, and the second molecule may be added to each of the wells W1 to W4.

Next, with all the valves kept closed, the wells W1 to W4 are irradiated with light from the light irradiation unit 83 to degrade the photodegradable linker of the second molecule, and thus the identifying portion and the labeling portion are detached and isolated (S1278).

Only the valve 1 is opened, and the liquid containing the identifying portion and the labeling portion isolated is transferred to the well of the second space (S1279). After that, the valve 1 is closed. The identifying portion recognizing molecule has been immobilized at the bottom surface of the well of the second space as described above; the identifying portion is bound specifically to the identifying portion recognizing molecule, and the labeling portion is detected and measured (S1279). By the measurement, what kind of cell-surface molecule is present on one cell to what degree can be identified and/or quantified. The measurement results may be stored as data in the memory unit 86.

(3) Embodiment 3

A case of using the first and second spaces different from Embodiment 2 will now be described. In this case, for example, the measurement of a cell secretion, the measurement of a cell-surface molecule, the preliminary amplification of an intracellular mRNA, or cell recovery can be performed.

For example, a cell secretion can be measured in the well of the first space, and the label of a cell-surface molecule can be measured in the well of the second space.

Also environment control by cell secretion stimulation or the like may be performed, and also the change in conditions of the cell may be measured.

In FIG. 14, a flow of the steps of Embodiment 3 after a chip for cell analysis is inserted into the apparatus for cell analysis is shown. The arrangement of wells of each space and the structure of the flow path and the valve are similar to those of the chip used in Embodiment 2 (FIG. 12). The first molecule that binds to a cell-surface molecule and an antibody that binds to a cell secretion are immobilized in the wells W1 to W4, and the identifying portion recognizing molecule is immobilized in the wells W5 to W8.

A description will now be given with reference to FIG. 14, FIG. 12, and FIG. 8.

First, on the basis of the memory based on the memory unit 86, the fluid control unit 81 is put into operation by the processing unit 82 to close the valve 1 and open the valves 3 to 5, and a liquid containing cells is introduced into the well W1 of the first space 11 and is passed in the direction from the well W1 to the well W4. One cell is trapped into each well by the first molecule (S1372). The unbound cells are removed by passing a cleaning liquid or the like (S1373).

Next, the environment of the trapped cell is controlled (S1374). For example, a cell secretion-stimulating substance that stimulates cell secretion is introduced by the fluid control unit 81. The cell secretion can be made active by the stimulating substance. At this time, the valves 3 to 5 may be opened to introduce the same stimulating substance, or the valves 3 to 5 may be closed to introduce a different stimulating substance to each well.

A cell secretion secreted to the outside of the cell is trapped by the antibody or the like immobilized at the bottom surface of the well of the first space, and is measured by the detection unit 85 (S1384). Thereby, what kind of cell secretion has been secreted from one cell to what degree can be identified and/or quantified. The measurement results may be stored as data in the memory unit 86.

The second molecule is bound to a cell-surface molecule of the cell trapped in the well of the first space (S1377). A specific type of or various cell-surface molecules can be labeled.

At this time, the fluid control unit 81 may be put into operation, and the valve 1 may be closed and the valves 3 to 5 may be opened to pass a liquid containing second molecules in the direction from the well W1 to the well W4, or all the valves may be closed to add a liquid containing second molecules to each of the wells W1 to W4.

Next, the wells W1 to W4 are irradiated with light by the light irradiation unit 83 to degrade the photodegradable linker of the second molecule, and thus the identifying portion and the labeling portion are detached and isolated (S1378). At this time, all the valves are closed.

With the valves 3 to 5 kept closed, the valve 1 is opened, and the liquid containing the identifying portion and the labeling portion isolated is transferred from the wells W2 to W4 of the first space 11 to the wells W6 to W8 of the second space 12 (S1379). After that, the valve 1 is closed.

The identifying portion recognizing molecule has been immobilized at the bottom surface of the well of the second space as described above; the identifying portion and the labeling portion isolated are trapped, and measurement is performed by the detection unit 85 (S1379). By the measurement, what kind of cell-surface molecule is present on one cell to what degree can be identified and/or quantified. The measurement results may be stored as data in the memory unit 86.

After that, a nucleic acid is acquired from the cell and is analyzed. In the case where a DNA or an mRNA of an intracellular molecule is preliminarily amplified, with all the valves kept closed, preliminary amplification by cell dissolution, the multi-displacement amplification method, etc. is performed (S1380), and the solution is recovered. The recovered solution may be used for the analysis of the DNA or the mRNA, etc.

It is also possible to perform steps (S1472 to 1479) similar to S1372 to S1379 of FIG. 14 and then recover the cell. The photodegradable linker of the first molecule is degraded by light irradiation, and thus the cell is isolated and recovered (S1481). The recovered cell may be used for culture etc.

(4) Embodiment 4

A case of using the first and second spaces different from Embodiments 2 and 3 will now be described. In this case, for example, the measurement of a cell secretion, the measurement of a cell-surface molecule, the preliminary amplification of an intracellular mRNA, or cell recovery can be performed.

For example, a cell secretion and a cell-surface molecule label may be measured in the well of the second space, and a DNA or an mRNA of an intracellular molecule may be measured in the well of the first space.

Also environment control by cell secretion stimulation or the like may be performed, and also the change in conditions of the cell may be measured.

In FIG. 16, a flow of the steps of Embodiment 4 after a chip for cell analysis is inserted into the apparatus for cell analysis is shown. The arrangement of wells of each space and the structure of the flow path and the valve are similar to those of the chip used in Embodiment 2 (FIG. 12). The first molecule that binds to a cell-surface molecule is immobilized in the wells W1 to W4, and an antibody that binds to a cell secretion and the identifying portion recognizing molecule are immobilized in the wells W5 to W8.

First, on the basis of the memory based on the memory unit 86, the fluid control unit 81 is put into operation by the processing unit 82 to close the valve 1 and open the valves 3 to 5, and a liquid containing cells is introduced into the well W1 of the first space 11 and is passed in the direction in the well W4 direction. One cell is trapped into each well by the first molecule (S1572). The unbound cells are removed by passing a cleaning liquid or the like (S1573).

Next, the environment of the trapped cell is controlled (S1574). For example, a cell secretion-stimulating substance that stimulates cell secretion is introduced by the fluid control unit 81. The cell secretion can be made active by the stimulating substance. At this time, the valves 3 to 5 may be opened to introduce the same stimulating substance, or the valves 3 to 5 may be closed to introduce a different stimulating substance to each well.

The valves 3 to 5 are closed and the valve 1 is opened, and a cell secretion secreted to the outside of the cell is transferred to the well of the second space (S1575). After that, all the valves are closed.

An antibody that binds specifically to the cell secretion has been immobilized at the bottom surface of the well of the second space 12 as described above; the transferred cell secretion is trapped, and is measured by the detection unit 85 (S1576). By the measurement, what kind of cell secretion has been secreted from one cell to what degree can be identified and/or quantified. The measurement results may be stored as data in the memory unit 86.

Next, the second molecule is bound to a cell-surface molecule of the cell trapped in the well of the first space 11 (S1577). A specific type of or various cell-surface molecules can be labeled.

At this time, the fluid control unit 81 may be put into operation, and the valve 1 may be closed and the valves 3 to 5 may be opened to pass a liquid containing second molecules in the direction from the well W1 to the well W4, or all the valves may be closed to add a liquid containing second molecules to each of the wells W1 to W4.

Next, all the valves are closed and the wells W1 to W4 are irradiated with light, and thus the identifying portion and the labeling portion are detached and isolated from the second molecule (S1578).

The valve 1 is opened, and the identifying portion and the labeling portion isolated are transferred to the well of the second space (S1579). After that, the valve 1 is closed.

The identifying portion and the labeling portion transferred are trapped by the identifying portion recognizing molecule immobilized at the bottom surface of the well of the second space, and measurement is performed by the detection unit 85 (S1579). By the measurement, what kind of cell-surface molecule is present on one cell to what degree can be identified and/or quantified. The measurement results may be stored as data in the memory unit 86.

After that, a nucleic acid is acquired from the cell and is analyzed. In the case where a DNA or an mRNA of an intracellular molecule is preliminarily amplified, with all the valves kept closed, preliminary amplification by cell dissolution, the multi-displacement amplification method, etc. is performed (S1580), and the solution is recovered. The recovered solution may be used for the analysis of the DNA or the mRNA, etc.

It is also possible to perform steps (S1672 to S1679) similar to S1572 to S1579 of FIG. 16 and then recover the cell. The light irradiation unit 83 is put into operation to degrade the photodegradable linker of the first molecule, and thus the cell is isolated and recovered (S1681). The recovered cell may be used for culture etc.

(5) Embodiment 5

A case of using the first and second spaces different from Embodiments 2 to 4 will now be described. In this case, for example, the measurement of a cell secretion, the measurement of a cell-surface molecule, the preliminary amplification of an intracellular mRNA, or cell recovery can be performed.

For example, a cell secretion and a cell-surface molecule label may be measured in the well of the second space, and a protein etc. of intracellular molecules may be measured in the well of the first space.

Also environment control by cell secretion stimulation or the like may be performed, and also the change in conditions of the cell may be measured.

In FIG. 18, a flow of Embodiment 5 after a chip for cell analysis is inserted into the apparatus for cell analysis is shown. The arrangement of wells of each space, the flow path, and the valve are similar to those of the chip used in Embodiment 2 (FIG. 12); the first molecule that binds to a cell-surface molecule is immobilized in the wells W1 to W4, and an antibody that binds specifically to a cell secretion and the identifying portion recognizing molecule are immobilized in the wells W5 to W8.

First, on the basis of the memory based on the memory unit 86, the fluid control unit 81 is put into operation by the processing unit 82 to close the valve 1 and open the valves 3 to 5, and a liquid containing cells is introduced into the well W1 of the first space; and one cell is trapped into each well by the first molecule (S1772). Thereby, the cell to be analyzed can be retained in the well.

The unbound cells are removed by passing a cleaning liquid or the like (S1773).

Next, the environment of the trapped cell is controlled (S1774). For example, a cell secretion-stimulating substance that stimulates cell secretion is introduced by the fluid control unit 81. The cell secretion can be made active by the stimulating substance. At this time, the valves 3 to 5 may be opened to introduce the same stimulating substance, or the valves 3 to 5 may be closed to introduce a different stimulating substance to each well.

The valves 3 to 5 are closed and the valve 1 is opened, and a cell secretion secreted to the outside of the cell is transferred to the well of the second space 12 (S1775). After that, the valve 1 is closed.

An antibody that binds specifically to the cell secretion has been immobilized at the bottom surface of the well of the second space 12 as described above; the transferred cell secretion is trapped, and is measured by the detection unit 85 (S1776). By the measurement, what kind of cell secretion has been secreted from one cell to what degree can be identified and/or quantified. The measurement results may be stored as data in the memory unit 86.

Next, the second molecule is bound to a cell-surface molecule of the cell trapped in the well of the first space 11 (S1777). A specific type of or various cell-surface molecules can be labeled. At this time, the valve 1 may be closed and the valves 3 to 5 may be opened by the fluid control unit 81 to pass a liquid containing second molecules in the direction from the well W1 to the well W4, or all the valves may be closed to add a liquid containing second molecules to each of the wells W1 to W4.

All the valves are closed and the wells W1 to W4 are irradiated with light from the light irradiation unit 83, and thus the identifying portion and the labeling portion of the second molecule are detached and isolated (S1778).

Only the valve 1 is opened, and the identifying portion and the labeling portion isolated are transferred to the well of the second space (S1779). After that, the valve 1 is closed.

The identifying portion and the labeling portion transferred are trapped by the identifying portion recognizing molecule immobilized at the bottom surface of the well of the second space, and measurement is performed by the detection unit 85 (S1779). By the measurement, what kind of cell-surface molecule is present on one cell to what degree can be identified and/or quantified. The measurement results may be stored as data in the memory unit 86.

After that, with all the valves kept closed, the cell is subjected to cell membrane permeation treatment and then subjected to intracellular staining (FISH etc.) (S1785), and intracellular imaging measurement is performed (S1786). The obtained image and the measurement results of the cell secretion mentioned above and the cell-surface molecule mentioned above may be used in combination; thus, the cell can be analyzed.

(6) Embodiment 6

A case of using the first, second, and third spaces will now be described. In this case, for example, the measurement of a cell secretion, the measurement of a cell-surface molecule, the preliminary amplification of an intracellular mRNA, or cell recovery can be performed. A cell secretion may be measured in the first space, a cell-surface molecule label may be measured in the second space, and a cell secretion secreted to the outside of the cell and a cell-surface molecule label may be measured in the third space.

Also environment control by cell secretion stimulation or the like may be performed, and also the change in conditions of the cell may be measured.

An overview of a chip for cell analysis is shown in FIG. 19.

Four wells W1 to W4 of the first space 11 are arranged longitudinally on the center, wells W5 to W8 of the second space 12 are arranged on the right side, and four wells W9 to W12 of a third space 13 are arranged longitudinally on the left side. The wells of each space are linked longitudinally by the flow path 16. Also the wells of the first space and the second space and the wells of the first space and the third space are linked transversely by the flow path 16 except for the wells at the upper end (W1, W5, and W9). The flow path 16 is provided with valves 1, 2, 3, 4, and 5.

The first molecule and an antibody corresponding to a cell secretion are immobilized in the wells W1 to W4, and the identifying portion recognizing molecule is immobilized in the wells W5 to W8.

The wells W1, W5, and W9 may be used as an inlet of cells, cleaning liquids, reagents, etc., or may be used as a control for measurement etc. of trapped cells, immobilized antibodies, etc.

In FIG. 20, a flow of Embodiment 6 after the chip for cell analysis is inserted into the apparatus for cell analysis is shown. A description will now be given with reference to FIG. 19, FIG. 20, and FIG. 8.

First, on the basis of the memory based on the memory unit 86, the fluid control unit 81 is put into operation by the processing unit 82 to close the valves 1 and 2 and open the valves 3 to 5, and a liquid containing cells is introduced into the well W1 of the first space and is passed in the direction from the well W1 to the well W4. During the passing, one cell is trapped by the first molecule in each of the wells W1 to W4 (S1972). Thereby, the cell to be analyzed can be retained in the well.

The unbound cells are removed by passing a cleaning liquid or the like (S1973).

Next, the environment of the trapped cell is controlled. For example, a cell secretion-stimulating substance that stimulates cell secretion is introduced by the fluid control unit 81 (S1974). The cell secretion can be made active by the stimulating substance. At this time, the valves 3 to 5 may be opened to introduce the same stimulating substance, or the valves 3 to 5 may be closed to introduce a different stimulating substance to each well.

All the valves are closed, and a cell secretion secreted to the outside of the cell is trapped by the antibody immobilized at the bottom surface of the well of the first space, and is measured by the detection unit 85 (S1984). By the measurement, what kind of cell secretion has been secreted from one cell to what degree can be identified and/or quantified. The measurement results may be stored as data in the memory unit 86.

Next, the second molecule is bound to a cell-surface molecule of the cell trapped (S1977). A specific type of or various cell-surface molecules can be labeled. At this time, the valve 1 may be closed and the valves 3 to 5 may be opened to pass a liquid containing second molecules in the direction from the well W1 to the well W4, or all the valves may be closed to add a liquid containing second molecules to each of the wells W1 to W4.

All the valves are closed and the wells W1 to W4 are irradiated with light by the light irradiation unit 83 to degrade the photodegradable linker of the second molecule, and thus the identifying portion and the labeling portion are detached and isolated (S1978).

The valve 1 is opened, and the liquid containing the identifying portion and the labeling portion isolated is transferred to each well of the second space 12. After that, the valve 1 is closed.

The identifying portion and the labeling portion transferred are trapped by the binding of the identifying portion recognizing molecule immobilized at the bottom surface of the well of the second space 12 and the identifying portion, and measurement is performed by the detection unit 85 (S1987). By the measurement, what kind of cell-surface molecule is present on one cell to what degree can be identified and/or quantified. The measurement results may be stored as data in the memory unit 86.

Next, all the valves are closed and the cell trapped in the wells W1 to W4 of the first space 11 is irradiated with light by the light irradiation unit 83, and thus the photodegradable linker of the first molecule is degraded and isolated (S1988).

Only the valve 2 is opened, and the isolated cell is transferred to the wells W8 to W12 of the third space 13 (S1989). After that, the valve 2 is closed.

The cell is dissolved in the well of the third space 13 (S1989). The dissolution may be performed by the addition of a solution, ultrasonic disintegration, etc.

Here, with all the valves kept closed, a DNA, an mRNA, etc. are preliminarily amplified by the multi-displacement amplification method or the like, as necessary.

The solution containing the amplified DNA or mRNA is recovered (S1990), and is analyzed by PCR, an NGS (next-generation sequencer), etc.

(7) Embodiment 7

A case of using the first, second, and third spaces different from Embodiment 6 will now be described. An overview of a chip for cell analysis is shown in FIG. 21.

With reference to FIG. 21, three wells W2 to W4 of the first space 11 are arranged longitudinally on the center, wells W5 to W8 of the second space 12 are arranged on the right side, and four wells W9 to W12 of the third space 13 are arranged longitudinally on the left side. The wells of the second and third spaces are linked longitudinally by the flow path 16, and the wells of the first space and the second space and the wells of the first space and the third space are linked transversely by the flow path 16 except for the wells at the upper end. The flow path is provided with valves 1, 2, 3, 4, and 5.

The first molecule that binds to a cell-surface molecule is immobilized in the wells W2 to W4, the identifying portion recognizing molecule is immobilized in the wells W5 to W8, and an antibody that binds specifically to a cell secretion is immobilized in the wells W9 to W12.

The wells W5 and W9 may be used as an inlet of cleaning liquids, reagents, etc., or may be used as a control for measurement etc. of reagents, immobilized antibodies, etc.

First, the fluid control unit 81 is put into operation to close all the valves and a liquid containing cells is introduced into the wells W2, W3, and W4 of the first space 11, and one cell is trapped by the first molecule immobilized in the well. Thereby, the cell to be analyzed can be retained in the well.

The second molecule composed of an antibody, a photodegradable linker, and a labeled nucleic acid fragment is introduced into the well, and is bound to a cell-surface molecule of the cell. Thereby, a sandwich of the first molecule, the cell, and the second molecule is formed.

Next, the wells W2 to W4 are irradiated with light by the light irradiation unit 83, and the labeled nucleic acid fragment (the identifying portion and the labeling portion) of the second molecule is isolated.

Only the valve 1 is opened, and the isolated labeled nucleic acid fragment is transferred to the wells W6 to W8 of the second space, and is bound specifically to a complementary nucleic acid fragment (the identifying portion recognizing molecule) immobilized in the wells W6 to W8.

The unbound labeled nucleic acid fragment is washed down and removed by opening the valves 3, 4, and 5 and passing a cleaning liquid or the like, and then signal amplification is performed and measurement is performed by the detection unit 85. By the measurement, what kind of cell-surface molecule is present on one cell to what degree can be identified and/or quantified. The measurement results may be stored as data in the memory unit 86.

In the case where a cell secretion is further measured, the fluid control unit 81 is used to introduce a cell secretion-stimulating substance into the wells W2 to W4 of the first space 11 in which cells are trapped. The cell secretion can be made active by the stimulating substance.

When a cell secretion is secreted, only the valve 2 is opened, and the secretion is transferred to the wells W10 to W12 of the third space 13 and is bound to the antibody that binds specifically to the cell secretion and is immobilized in the well. The unbound secretion is removed by opening the valves 3, 4, and 5.

All the valves are closed, and signal amplification is performed and measurement is performed by the detection unit 85. By the measurement, what kind of cell secretion has been secreted from one cell to what degree can be identified and/or quantified. The measurement results may be stored as data in the memory unit 86.

(8) Embodiment 8

A case of using the first, second, and third spaces different from Embodiments 6 and 7 will now be described. The arrangement of wells of each space, the flow path, and the valve are similar to those of the chip used in Embodiment 6 (FIG. 19). The first molecule is immobilized in the well of the first space 11, the identifying portion recognizing molecule is in the well of the second space 12, and an antibody that binds specifically to a cell secretion is in the well of the third space 13.

First, on the basis of the memory based on the memory unit 86, the fluid control unit 81 is put into operation by the processing unit 82 to close the valves 1 and 2 and open the valves 3 to 5, and a liquid containing cells is introduced into the well W1 of the first space 11; while the liquid is passed from the well W1 to the well W4, one cell is trapped into each well by the first molecule. Thereby, the cell to be analyzed can be retained in the well.

The second molecule composed of an antibody, a photo-degradable linker, and a labeled nucleic acid fragment is introduced into the well by the fluid control unit 81, and is bound to a cell-surface molecule of the cell. Thereby, a sandwich of the first molecule, the cell, and the second molecule is formed.

The unbound second molecules are washed down and removed by a cleaning liquid or the like.

All the valves are closed and the wells W1 to W4 of the first space 11 are irradiated with light, and thus the labeled nucleic acid fragment of the second molecule is isolated. Only the valve 1 is opened, and the isolated labeled nucleic acid fragment is transferred from the wells W2 to W4 of the first space 11 to the wells W6 to W8 of the second space 12.

The valve 1 is closed, and the transferred labeled nucleic acid fragment is bound specifically to a complementary nucleic acid fragment immobilized in the well of the second space 12. Thereby, a double-strand nucleic acid fragment is formed. After that, the valves 3 to 5 are opened, and the unbound labeled nucleic acid fragment is washed down and removed by a cleaning liquid or the like.

All the valves are closed, and signal amplification is performed and then the measurement of each well of the second space 12 is performed by the detection unit 85. By the measurement, what kind of cell-surface molecule is present on one cell to what degree can be identified and/or quantified. The measurement results may be stored as data in the memory unit 86.

In the case where a cell secretion is further measured, the fluid control unit 81 is used to close all the valves or to close the valves 1 and 2 and at the same time open the valves 3 to 5, and a cell secretion-stimulating substance is introduced into the well of the first space 11 in which trapped cells are present. The cell secretion can be made active by the stimulating substance.

Next, the valves 1 and 3 to 5 are closed and the valve 2 is opened, and a cell secretion secreted to the outside of the cell is transferred to the wells W10 to W12 of the third space 13. Then, the cell secretion is bound to the antibody that binds specifically to the cell secretion and is immobilized in the well of the third space. The unbound cell secretion is removed by closing the valves 1 and 2, opening the valves 3 to 5, and passing a cleaning liquid or the liker. After that, all the valves are closed, and signal amplification is performed and measurement is performed by the detection unit 85. By the measurement, what kind of cell secretion has been secreted from one cell to what degreed can be identified and/or quantified. The measurement results may be stored as data in the memory unit 86.

Further, a nucleic acid may be acquired from the cell and analyzed. In the case where an intracellular molecule (DNA or mRNA) is amplified, all the valves are closed, and the cell trapped in the first space is dissolved. The dissolution may be performed by the introduction of a dissolving liquid, ultrasonic disintegration, etc.

Next, preliminary amplification is performed by the multi-displacement amplification method or the like, and the liquid is recovered and analyzed by PCR, NGS, etc.

In the case where the cell is recovered separately from this, all the valves are closed, and each well of the first space 11 is irradiated with light. The recovered cell is used for culture etc.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

1. A method for analyzing a cell comprising:
(A) trapping the cell by binding a first molecule to the cell;
(B) binding a second molecule to the cell, the second molecule including:
a binding portion capable of specific binding to a cell-surface molecule of the cell; an identifying portion;
a labeling portion coupled to the identifying portion; and
a stimulus-degradable linker between the binding portion and the identification portion;
(C) detaching the identifying portion from the binding portion by stimulating the stimulus-degradable linker, wherein the detached identifying portion is coupled to the labeling portion;
(D) binding the detached identifying portion through specific binding to an identifying portion recognizing molecule; and
(E) detecting the labeling portion.

(2) The method for analyzing a cell according to claim (1), further comprising:
(F) identifying and/or quantifying the cell-surface molecule of the cell by as a result of detecting the labeling portion.

(3) The method for analyzing a cell according to claim (1), further comprising:
(G) identifying and/or quantifying a cell secretion from the cell; and/or
(H) acquiring a nucleic acid from the cell and analyzing the nucleic acid.

(4) The method for analyzing a cell according to claim (1), wherein the cell is a single cell or a plurality of cells of the same type.

(5) The method for analyzing a cell according to claim (1), wherein the first molecule includes an oleyl group, an antibody, an aptamer, or a molecular recognition polymer.

(6) The method for analyzing a cell according to claim (1), wherein the first molecule is immobilized to a well and the first molecule includes a stimulus-degradable linker between a portion capable of binding to the cell and the well.

(7) The method for analyzing a cell according to claim (1), wherein the second molecule includes an antibody, an aptamer, or a molecular recognition polymer.

(8) The method for analyzing a cell according to claim (1), wherein the stimulus-degradable linker is a photodegradable linker.

(9) The method for analyzing a cell according to claim (1), wherein the stimulus-degradable linker is a photocleavable linker.

(10) The method for analyzing a cell according to claim (1), wherein the identifying portion includes a nucleic acid fragment.

(11) The method for analyzing a cell according to claim (10), wherein the identifying portion recognizing molecule includes a nucleic acid fragment complementary to the nucleic acid fragment included in the identifying portion.

(12) The method for analyzing a cell according to claim (1), wherein the identifying portion recognizing molecule is immobilized to a well.

(13) The method for analyzing a cell according to claim (12), wherein a position of the identifying portion recognizing molecule in the well provides information about the cell.

(14) A chip for cell analysis comprising:
a first region where a first molecule capable of binding to a cell is immobilized;
a second region where an identifying portion recognizing molecule is immobilized, wherein the identifying portion recognizing molecule is capable of binding specifically to a second molecule having an identifying portion and a labeling portion that identify information about the cell; and
a detection region configured to detect the labeling portion.

(15) The chip for cell analysis according to claim (14), further comprising:
a first well having a region selected from the group consisting of the first region, the second region, and the detection region;
a flow path making a link between the first well and a second well; and
a valve provided at the flow path.

(16) The chip for cell analysis according to claim (15), wherein an identifying portion recognizing molecule and/or a cell secretion recognizing molecule is immobilized in the first well.

(17) The chip for cell analysis according to claim (16), wherein the identifying portion recognizing molecule and/or the cell secretion recognizing molecule includes a plurality of types of molecules.

(18) The chip for cell analysis according to claim (17), wherein a position of the identifying portion recognizing molecule and/or the cell secretion recognizing molecule in the first well provides information about the cell.

(19) A reagent for cell analysis comprising:
a molecule including:
a binding portion capable of binding specifically to a molecule selected from the group consisting of a cell-surface molecule, an intracellular molecule, and a cell secretion;
an identifying portion;
a labeling portion coupled to the identifying portion; and
a stimulus-degradable linker between the binding portion and the identification portion.

(20) A kit for cell analysis comprising:
a chip for cell analysis including:
a first region where a first molecule capable of binding to a cell is immobilized,
a second region where a molecule capable of binding specifically to a second molecule in which a binding portion capable of binding specifically to the cell, an identifying portion, and a labeling portion are linked is immobilized, and
a detection region where the labeling portion is able to be detected; and
a reagent selected from the group consisting of a reagent containing a molecule including a binding portion capable of binding specifically to a molecule selected from the group consisting of a cell-surface molecule, an intracellular molecule, and a cell secretion and a labeling portion, a reagent that detects the labeling portion of the preceding reagent, and a reagent containing a substance that stimulates cell secretion.

(21) An apparatus for cell analysis comprising:
an insertion unit configured to insert the chip for cell analysis of claim 14;
a fluid control unit configured to control a movement of a fluid within the chip for cell analysis of claim 14;
a light irradiation unit configured to apply light to the first region of the chip for cell analysis of claim 14; and a detection unit configured to detect the labeling portion in the detection region of the chip for cell analysis of claim 14.

REFERENCE SIGNS LIST 1 to 5 valve
11 first space
12 second space
13 third space
16 flow path
21 first molecule
22 cell
23 cell-surface molecule
24 second molecule
25 stimulus-degradable linker
26, 31 well
27 metal
28 nucleic acid fragment
29 fluorescently labeled substance
32 identifying portion recognizing molecule for cell-surface molecule measurement
33 identifying portion recognizing molecule for intracellular molecule measurement
34 spot
61 light
81 fluid control unit
82 processing unit
83 light irradiation unit
84 insertion unit
85 detection unit
86 memory unit
87 apparatus for cell analysis

The invention claimed is:

1. A method for analyzing a cell comprising:
(A) trapping the cell by binding a first molecule to the cell, wherein the first molecule is immobilized to a chip and comprises a cell-binding portion capable of binding to the cell;
(B) binding a second molecule to the cell, the second molecule comprising:
a binding portion capable of specific binding to a cell-surface molecule of the cell;
an identifying portion;
a labeling portion coupled to the identifying portion; and
a stimulus-degradable linker between the binding portion and the identifying portion;
(C) detaching the identifying portion from the binding portion by stimulating the stimulus-degradable linker, wherein the detached identifying portion is coupled to the labeling portion;
(D) binding the detached identifying portion through specific binding to an identifying portion recognizing molecule immobilized to the chip; and
(E) detecting the labeling portion coupled to the detached identifying portion bound to the identifying portion recognizing molecule.

2. The method for analyzing a cell according to claim 1, further comprising:
(F) identifying and/or quantifying the cell-surface molecule of the cell based on a result of detecting the labeling portion.

3. The method for analyzing a cell according to claim 1, further comprising:
(G) identifying and/or quantifying a cell secretion from the cell; and/or (H) acquiring a nucleic acid from the cell and analyzing the nucleic acid.

4. The method for analyzing a cell according to claim 1, wherein the cell is a single cell or a plurality of cells of a same type.

5. The method for analyzing a cell according to claim 1, wherein the cell-binding portion comprises an oleyl group, an antibody, an aptamer, or a molecular recognition polymer.

6. The method for analyzing a cell according to claim 1, wherein the first molecule is immobilized to a well of the chip and the first molecule includes a stimulus-degradable linker between the cell-binding portion of the first molecule and the well.

7. The method for analyzing a cell according to claim 1, wherein the second molecule comprises an antibody, an aptamer, or a molecular recognition polymer.

8. The method for analyzing a cell according to claim 1, wherein the stimulus-degradable linker is a photodegradable linker.

9. The method for analyzing a cell according to claim 1, wherein the stimulus-degradable linker is a photocleavable linker.

10. The method for analyzing a cell according to claim 1, wherein the identifying portion comprises a nucleic acid fragment.

11. The method for analyzing a cell according to claim 10, wherein the identifying portion recognizing molecule includes a nucleic acid fragment complementary to the nucleic acid fragment included in the identifying portion.

12. The method for analyzing a cell according to claim 1, wherein the identifying portion recognizing molecule is immobilized to a well of the chip.

13. The method for analyzing a cell according to claim 12, wherein a position of the identifying portion recognizing molecule in the well provides information on type of the cell-surface molecule.

* * * * *